(12) United States Patent
Black

(10) Patent No.: US 7,144,247 B2
(45) Date of Patent: Dec. 5, 2006

(54) HYGIENIC TREATMENTS OF STRUCTURES IN BODY CAVITIES

(75) Inventor: Michael Black, Foster City, CA (US)

(73) Assignee: Oralum, LLC, Foster City, CA (US)

( * ) Notice: Subject to any disclaimer, the term of this patent is extended or adjusted under 35 U.S.C. 154(b) by 461 days.

(21) Appl. No.: 10/424,114

(22) Filed: Apr. 25, 2003

(65) Prior Publication Data

US 2003/0232303 A1    Dec. 18, 2003

(51) Int. Cl.
*A61C 3/00* (2006.01)
*A61H 1/00* (2006.01)
*A61B 18/18* (2006.01)

(52) U.S. Cl. .............................. 433/29; 601/15; 606/3

(58) Field of Classification Search ................... 433/29; 601/15; 606/3, 11, 12; 607/79, 92, 94
See application file for complete search history.

(56) References Cited

U.S. PATENT DOCUMENTS

| | | | |
|---|---|---|---|
| 3,667,454 A | 6/1972 | Prince | 128/24.2 |
| 4,779,173 A | 10/1988 | Carr et al. | 362/109 |
| 4,930,504 A * | 6/1990 | Diamantopoulos et al. | 607/88 |
| 5,030,090 A | 7/1991 | Maeda et al. | 433/29 |
| 5,160,194 A | 11/1992 | Feldman | 362/109 |
| 5,176,130 A * | 1/1993 | Kim | 601/15 |
| 5,290,274 A | 3/1994 | Levy | 606/16 |
| 5,306,143 A | 4/1994 | Levy | 433/29 |
| 5,401,171 A | 3/1995 | Paghdiwala | 433/215 |
| 5,540,676 A * | 7/1996 | Freiberg | 606/3 |
| 5,611,793 A | 3/1997 | Wilson et al. | 606/2 |
| 5,658,148 A | 8/1997 | Neuberger et al. | 433/215 |
| 6,015,404 A | 1/2000 | Altshuler et al. | 606/9 |
| 6,026,828 A | 2/2000 | Altshuler | 132/311 |
| 6,056,548 A | 5/2000 | Neuberger et al. | 433/215 |
| 6,063,108 A * | 5/2000 | Salansky et al. | 607/89 |
| 6,080,146 A | 6/2000 | Altshuler et al. | 606/9 |
| 6,094,767 A | 8/2000 | Iimura | 15/105 |
| 6,202,242 B1 | 3/2001 | Salmon et al. | 15/22.1 |
| 6,270,342 B1 | 8/2001 | Neuberger et al. | 433/29 |

(Continued)

FOREIGN PATENT DOCUMENTS

WO    WO 99/52596    10/1999

OTHER PUBLICATIONS

Belikov, et al., "Investigation of IR Absorption Spectra of Oral Cavity Bacteria," SPIE, vol. 2922, pp. 113-118.

(Continued)

*Primary Examiner*—Todd E. Manahan
(74) *Attorney, Agent, or Firm*—Lumen Intellectual Property Services, Inc.

(57) ABSTRACT

Multiple hygienic effects are concurrently applied to structures of body cavities. This is established by two or more light sources each capable of delivering a light beam to the structures using optical pathways whereby each light beam provides a unique hygienic effect to the structures. The device could be a handheld device with detachable components. The device could include a massaging mechanism and/or a vibrating mechanism. An agent could be used to the body cavity to assist in the hygienic treatment plan. A cradle could be included to store the device, reload the power supply of the device, as well as a means to communicate with a hygienic service provider. The cradle could also host a display and a selector. A test mechanism could be included to test a performance of the device or to calibrate components of the device.

27 Claims, 23 Drawing Sheets

U.S. PATENT DOCUMENTS

| | | | |
|---|---|---|---|
| 6,273,884 B1 | 8/2001 | Altshuler et al. | 606/9 |
| 6,290,496 B1 | 9/2001 | Azar | 433/29 |
| 6,443,915 B1* | 9/2002 | Hwang | 601/15 |
| 6,485,300 B1 | 11/2002 | Muller et al. | 433/29 |
| 6,508,813 B1 | 1/2003 | Altshuler | 606/9 |
| 6,511,475 B1 | 1/2003 | Altshuler et al. | 606/9 |
| 6,517,532 B1 | 2/2003 | Altshuler et al. | 606/9 |
| 6,537,302 B1* | 3/2003 | Thiberg | 607/88 |
| 6,558,372 B1 | 5/2003 | Altshuler | 606/2 |
| 6,561,808 B1 | 5/2003 | Neuberger | 433/215 |
| 6,569,156 B1 | 5/2003 | Tankovich et al. | 606/10 |
| 6,571,049 B1* | 5/2003 | Nath | 385/139 |
| 6,602,275 B1* | 8/2003 | Sullivan | 607/88 |
| 6,613,042 B1 | 9/2003 | Tankovich et al. | 606/10 |
| 6,616,451 B1* | 9/2003 | Rizolu et al. | 433/215 |
| 6,666,878 B1 | 12/2003 | Carlgren | 607/91 |
| 6,702,837 B1* | 3/2004 | Gutwein | 607/88 |
| 6,758,844 B1 | 7/2004 | Neuberger | 303/3 |
| 6,896,693 B1* | 5/2005 | Sullivan | 607/91 |
| 6,902,397 B1* | 6/2005 | Farrell et al. | 433/29 |
| 2002/0061495 A1* | 5/2002 | Mault | 433/215 |
| 2002/0128635 A1 | 9/2002 | Altshuler et al. | |
| 2002/0173780 A1 | 11/2002 | Altshuler et al. | |
| 2003/0032900 A1* | 2/2003 | Ella | 601/6 |
| 2003/0055413 A1 | 3/2003 | Altshuler et al. | |
| 2003/0055414 A1 | 3/2003 | Altshuler et al. | |
| 2003/0065314 A1 | 4/2003 | Altshuler et al. | |
| 2003/0093915 A1 | 5/2003 | Pearl et al. | 34/96 |
| 2003/0113685 A1* | 6/2003 | Plank et al. | 433/29 |
| 2003/0163068 A1* | 8/2003 | Kang | 601/15 |
| 2004/0049247 A1 | 3/2004 | Perricone | 607/88 |
| 2004/0053190 A1* | 3/2004 | Lin | 433/29 |
| 2004/0193236 A1 | 9/2004 | Altshuler et al. | 607/88 |
| 2005/0053106 A1* | 3/2005 | Herron et al. | 372/38.07 |

OTHER PUBLICATIONS

"Everything for Love the Tingler, Head Massager," www.drugstore.com.

http://www.karna-ddscomfordent.com/basics.html, "Basics of the Biolase Millennium Hydrokinetic (HKS) Hard/Soft Tissue Laser and Clinical Cases.".

http://www.igiaonline.com/iglaztootwhi.html, "IGIA Lazer-White Tooth Whitening."

GA Askaryan, "The Biological Media," Kvantovaya Electronika, V9(N7):1370-1383).

* cited by examiner

HYGIENIC TREATMENTS OF STRUCTURES IN BODY CAVITIES

FIELD OF THE INVENTION

This invention relates generally to hygienic devices, methods and systems. More particularly, the present invention relates to the application of two or more hygienic effects to structures in a body cavity.

BACKGROUND

Hygiene relates to the principles of cleanliness, promotion and preservation of health or the freeing from disease-causing microorganisms. Hygienic effects can be established in different ways of which one is through the effect of light on biological structures. For instance, the hygienic effect of visible, near ultraviolet and infrared light on biological structures is well known and has been described to provide anti-inflammatory effects, preventative effects, caries-protective effects, anti-bacterial effects, sterilizing effects, cleaning effects, cosmetic effects, therapeutic effects, healing effects (bio-stimulative effects), bio-altering effects, pain-releaving effects, agent-penetrating effects, photo-rejunivating effects and photo-dynamic treatment effects (See for instance a book by Goldman (1981) entitled "*The biomedical laser: technology and clinical applications*" and published by Springer-Verlag, New York; a book by Katzir (1993) entitled "*Lasers and optical fibers in medicine*" and published by Academic Press, New York; a book by Hajder et al. (1994) entitled "*Acupuncture and lasers*" and published by Ming, Belgrade; a book by Tuner et al. (1996) entitled "*Laser therapy in dentistry and medicine*" and published by Prisma Books, Grangesberg, Sweden; a book by Alster et al. (1996) entitled "*Cosmetic laser surgery*" and published by Wiley & Sons, New York; or a book by Fitzpatrick et al. (2000) entitled "*Cosmetic Laser Surgery*" and published by Mosby, St. Louis). The effects of a laser on biological structures is dependent on the laser properties (active matter, beam wavelength, continuous or impulse mode of operation), characteristics of the structures, water content, pigmentation degree, vascularization, vitality, heterogeneity, specific heat conductivity or time exposure. The photo-effect of a laser can be applied to superficial structures and subcutaneous structures. As far as the mechanisms of laser radiation effects are concerned, they may be thermal, mechanical or chemical.

When it comes to oral hygiene, the art teaches a wide variety of toothbrushes that include a light source aimed at providing a hygienic effect to the oral cavity, e.g. gums and teeth. These toothbrushes typically have a brush head and a light source. The light source illuminates through the bristles utilizing a certain transparency of the bristles or adjacent to the bristles. Even though these toothbrushes have the best of intentions by adding a hygienic effect to the daily exercise of tooth brushing, they cannot guarantee that the hygienic effect is actually applied to the gums or teeth. For instance, the use of toothpaste would partially or sometimes completely obstruct the penetration of the light beam, which would make the actual application of the light beam to the gums or teeth unknown and unreliable. If one assumes that the hygienic effect could in fact be reliably applied, then the current toothbrushes are still restricted to one single hygienic effect by selecting one light source that delivers radiation at one wavelength for each toothbrush. Unfortunately, the use of a single toothbrush that provides a single hygienic effect would not satisfy a much more inclusive hygienic maintenance of an oral cavity in which multiple hygienic effects would be desired. Accordingly, there is a need to provide new hygienic devices and methods that would satisfy a much more inclusive application of multiple hygienic effects for oral cavities and body cavities in general.

SUMMARY OF THE INVENTION

The present invention overcomes the shortcomings in the prior art by providing multiple hygienic effects that can be applied to structures in body cavities in a concurrent fashion. This is established by two or more light sources each capable of delivering a light beam to the structures whereby each light beam provides a unique hygienic effect to the structures. The preferred light source is a low power light source, including light emitting diodes or semiconductor lasers, capable of delivering light from the ultraviolet, visible or infrared spectrum. An optical means is used to apply the light beam to the structures, after which the structures concurrently receive said unique hygienic effects. The optical means could include one or more optical components such as optical fibers, lenses, spectral filters, mirrors, transparent materials, semi-transparent materials, prisms, reflective coatings, reflecting grooves, beam splitters, collimators, light channels or gratings.

Dependent on the type of structure and body cavity various kinds of hygienic effects can be selected such as an anti-inflammatory effect, a preventative effect, a caries-protective effect, an anti-bacterial effect, a sterilizing effect, a cleaning effect, a cosmetic effect, a therapeutic effect, a healing effect, a bio-stimulative effect, a bio-altering effect, a pain-releaving effect, an agent penetrating effect, a photo-rejuvinating effect or a photo-dynamic treatment effect. In general, at least two of the same light sources could be used each delivering a unique hygienic effect or at least two different light sources could be used each delivering a unique hygienic effect. The desired hygienic effects that one would like to obtain guides the choice of light sources and its parameters. By varying parameters such as e.g. fluence, spot size, mode such as continuous or pulsed, repetition rate, pulse duration different hygienic effects could be established. The device could be used in a quasi-stationary manner or in a dynamic manner. In one aspect, the application of light beams at different locations in the body cavity is established through movement of the device. Blending of different unique hygienic effects could be achieved at different locations in the body cavity.

Examples of body cavities include an oral system, a nasal system, an ear, a rectal system, a vaginal system, a uterus, an open wound, or a surgically created body cavity. Structures include any type of microorganism (including disease-causing microorganisms), cell layers, tissues, organs or materials as well as any type of non-biological materials that are present in a body cavity including fillings, braces, medical assistive devices, medical preventive devices, or the like.

The device could further include a massaging means to massage the structures in the body cavity and improve the transparency to the light beams. The device could also include a vibrating means to vibrate the structures in the body cavity to provide additional or alternative massaging effects. Examples of a vibrating means include an ultrasonic means, a piezoelectric means or a mechanical means. The present invention could also include the application of an agent to the body cavity before, during or after the application of the hygienic treatment. Examples of agents are, for instance, bioprotective agents, photocatalyst, treatment gels or cream, soothing agents, skin permeation enhancers or the like.

The device could include a selection means for a user to select parameters related to the hygienic treatment. The device could further include a displaying means to display data related to hygienic treatment. A testing means could be included to test a performance of the device or to calibrate the components of the device. The results of such a test could result in an adjustment of some of the components of the device or could generate feedback. A communication means could be included to communicate data with a cell phone, a personal digital assistant, a Pocket PC, a computer, an Internet website, a professional or a service, which could act as a hygienic service provider. Such a communication allows data to be exchanged and evaluated to provide recommendations, updates on treatment plans, renewals of parameter definitions or treatment plans, or adjustments that are needed to provide a certain quality standard of the treatment plan. Furthermore, a list of hygienic effects could be provided either by the device or the hygienic service provider. Such a list could be of help to select, update renew or adjust the treatment plan. A feedback means could also be included to provide feedback to a user through sound, display or vibration or to provide feedback to a hygienic service provider.

The device of the present invention could be a handheld device. Furthermore, the device of the present invention could include several detachable components such as a detachable handle and a detachable head. The detachable head includes an optical means to generate and deliver the light beams to the structures. The head could be split up into at least two other detachable components. A first component that could include the light sources to generate the light beams and a second component that could include means to guide and output the light beams to the structures. All these components could be disposable components. A cradle could be included to store the device, reload the power supply of the device, as well as a means to communicate with a hygienic service provider and/or testing means. The cradle could also host the displaying means and selecting means.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Figure 1:
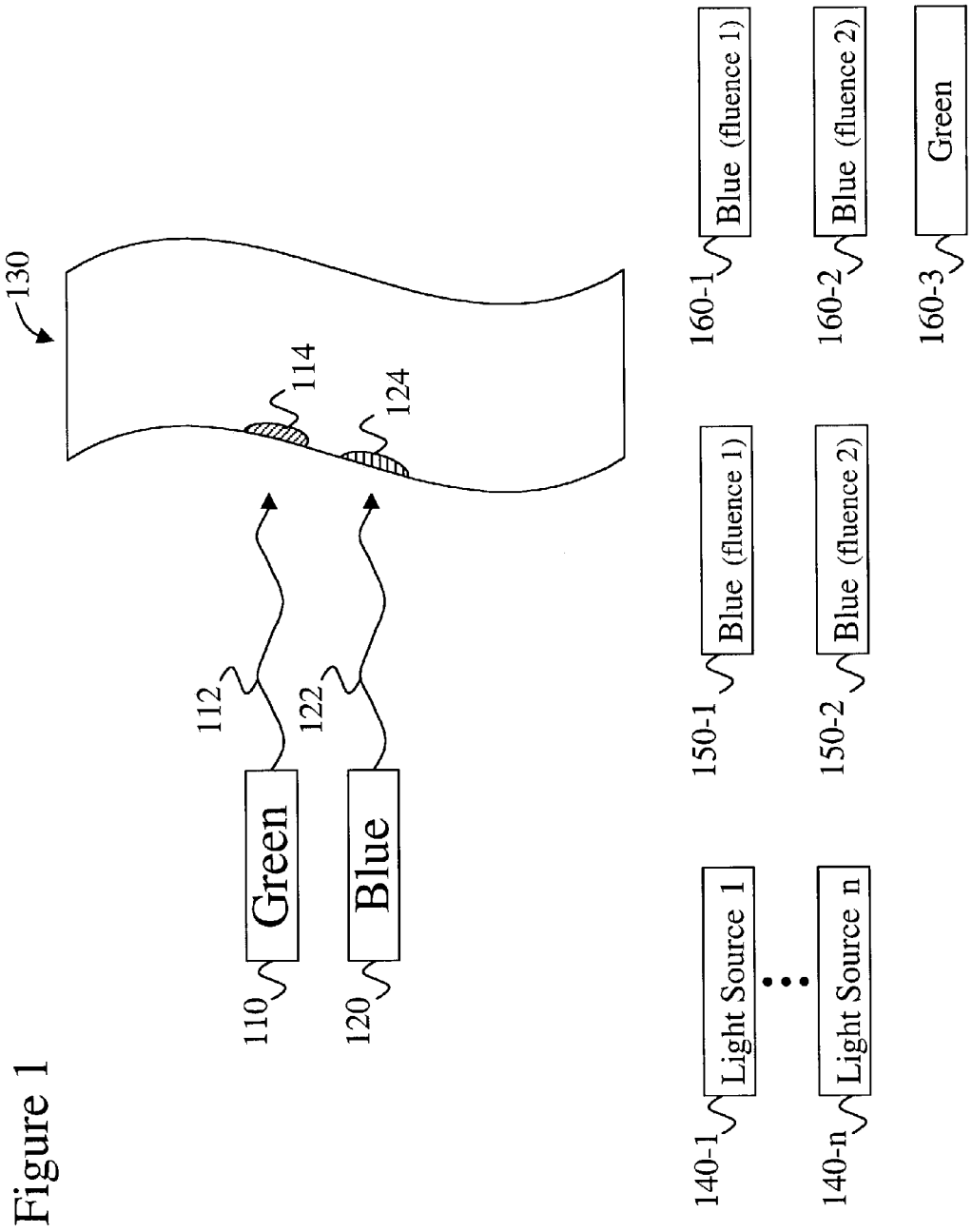
FIGS. 1–2 show examples of applying hygienic effects to structures in a quasi-stationary manner according to the present invention.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides a device and method to concurrently apply two or more hygienic effects to structures in a body cavity. These hygienic effects are established by two or more light sources each capable of delivering a light beam with a unique hygienic effect to the structures in the body cavity. The application of the hygienic effects could be established either in a quasi-stationary manner or a dynamic manner. The light sources are preferably low power light sources including low power lasers, light emitting diodes or low power semiconductor lasers (See, for instance, the following companies which are listed for purposes of illustration and should not be regarded as limiting to the invention: Coherent Inc., Santa Clara, Calif.; Microlasers by PolyScientific Inc., Blackbury, Va.; Photonic Products, Bishops Stortford, United Kingdom; Organic LEDs by Covion Organic Semiconductors GmbH, Frankfurt, Germany; Blue light emission from porous silicon by University of Science and Technology of China in Hefei). In general, at least two of the same light sources could be used each delivering a unique hygienic effect or at least two different light sources could be used each delivering a unique hygienic effect. The desired hygienic effects that one would like to obtain guides the choice of light sources and its parameters. By varying parameters such as e.g. fluence, spot size, mode such as continuous or pulsed, repetition rate, pulse duration different hygienic effects could be established.

A body cavity is defined as any body cavity that was created in a natural way, created in an unhealthy way or created in an unnatural way. Examples of naturally created body cavities are the oral system or mouth, a nasal system or nose, an ear, a vaginal system, uterus or a rectal system. Examples of an unhealthy created body cavity are body cavities that are caused by disease or infections. Examples of unnaturally created body cavities are open wounds, gunshot wounds that created a cavity, open wounds inflicted by physical assault, burns that created a cavity, or surgically created body cavities, including body cavities created with an endoscope. A surgically created body cavity is, for instance, created by an incision through the skin such that the skin opening provides access to subcutaneous body cavities that might require hygienic treatment. Examples of surgically accessible body cavities include the cardio-vascular system, intestinal system, organs, or any other body cavities surrounding the organs or functional systems. Structures encompass any type of microorganism (including disease-causing microorganisms), cell layers, tissues, organs or materials as well as any type of non-biological materials that are present in a body cavity including fillings, braces, medical assistive devices, medical preventive devices, or the like.

In general, hygienic effects relate to the cleanliness of these structures, promotion and preservation of health of the structures or freeing the body cavity from disease-causing microorganisms. In particular, the present invention encompasses hygienic effects related to the hygienic effect of visible, near ultraviolet and infrared light on these structures, which are known in the art (for a light spectrum refer to page 13 in a book by Tuner et al. (1996) entitled "*Laser therapy in dentistry and medicine*" and published by Prisma Books, Grangesberg, Sweden). Examples of such hygienic effects that could be selected as the two or more hygienic effects include anti-inflammatory effects, preventative effects, caries-protective effects, anti-bacterial effects, sterilizing effects, cleaning effects, cosmetic effects, therapeutic effects, healing effects (bio-stimulative effects), bio-altering effects, pain-releaving effects, teeth whitening effects, photo-rejuvination effects, photodynamic effects or agent-penetration effects.

To establish a particular hygienic effect at a structure one needs to consider the light source properties such as the type of low power light source, wavelength of the light beam, the continuous or impulse mode of operation of the light sources, characteristics of the structures, water content of the structures, pigmentation degree of the structures, vascularization of the structures, vitality of the structures, heterogeneity of the structures, specific heat conductivity of the structures, the fluence of light penetration through a structure or the time exposure needed for the light beam. The art provides teachings on hygienic photo-effects of structures including guidelines regarding parameters such as the type of light source, selection of wavelength(s), fluence, penetration, selection of spot size, recommended pulse duration, recommended repetition rate, or the like. The selection of the two or more hygienic effects as part of the present invention incorporate these teachings as well as new teachings that become available in the art describing newly identified hygienic effects.

Currently available teachings are described in the following books, which provide an exemplary list rather than a comprehensive list. The list includes a book by Goldman (1981) entitled "*The biomedical laser: technology and clinical applications*" and published by Springer-Verlag, New York; a book by Katzir (1993) entitled "*Lasers and optical fibers in medicine*" and published by Academic Press, New York; a book by Hajder et al. (1994) entitled "*Acupuncture and lasers*" and published by Ming, Belgrade; a book by Tuner et al. (1996) entitled "*Laser therapy in dentistry and medicine*" and published by Prisma Books, Grangesberg, Sweden; a book by Alster et al. (1996) entitled "*Cosmetic laser surgery*" and published by Wiley & Sons, New York; or a book by Fitzpatrick et al. (2000) entitled "*Cosmetic Laser Surgery*" and published by Mosby, St. Louis).

FIG. 1 shows a first exemplary embodiment of two light sources 110, 120 delivering a light beam with a green wavelength 112 and a light beam with a blue wavelength 122, respectively. The green wavelength 112 and blue wavelength 122 each provide a unique hygienic effect when applied in a quasi-stationary manner to structure 130, which is part of a body cavity. In this example, both light beams 112, 122 have a fairly superficial hygienic effect at structure 130 as shown by 114, 124. In general, two or more light sources could be used such as n light source 140-1 to 140-n. As discussed supra, two of the same light sources could be used such as two light sources 150-1, 150-2 that each deliver blue light, however, with at least one different parameter to establish a different and unique hygienic effect for each of the two light sources 150-1, 150-2. Such as different and unique hygienic effect could be established by different fluences for each of the two light sources 150-1, 150-2, i.e. fluence 1 and fluence 2, respectively. Another example is that there are three light sources, of which two are the same 160-1, 160-2 and one 160-3 is different, though all three delivering a unique hygienic effect.

Figure 2:
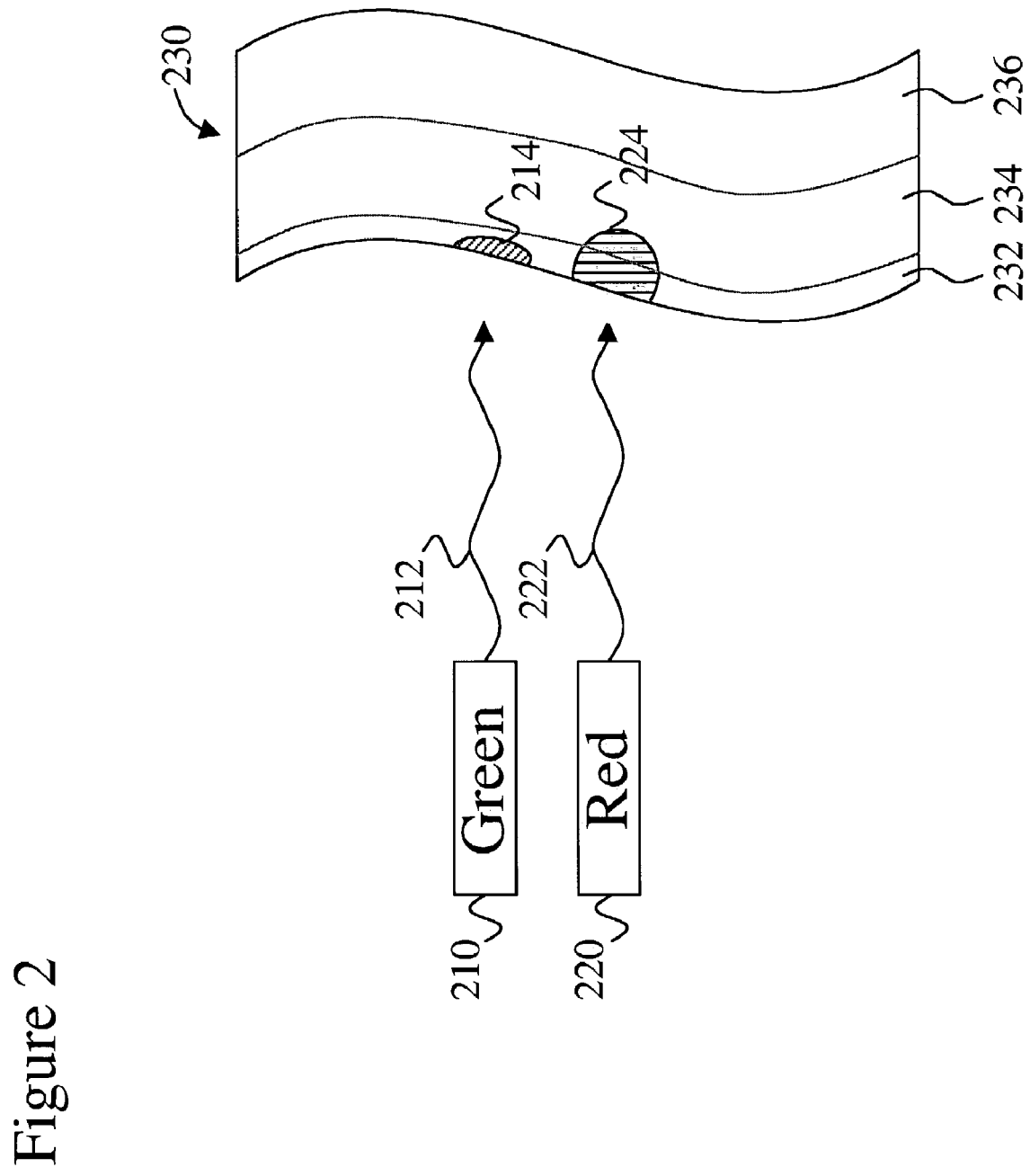

Structure 130 is shown as a structure with a homogenous consistency. However, most structures that one would encounter in a body cavity, as described supra, have a heterogeneous consistency or formation. FIG. 2 shows a second exemplary embodiment of two light sources 210, 220 delivering in a quasi-stationary manner a light beam with a green wavelength 212 and a light beam with a red wavelength 222, respectively to a heterogeneous structure 230, which is accessible through a body cavity. Structure 230 distinguishes three different layers, i.e. a superficial layer 232, a middle layer 234 and a deep layer 236. The green wavelength 212 and red wavelength 222 each provide a unique hygienic effect when applied at structure 230. Light beam 212 has a superficial hygienic effect as shown by 214, which is similar to the example in FIG. 1. However, light beam 222 has a hygienic effect in superficial layer 232 that extends to part of middle layer 234. In other words, the red wavelength penetrates deeper in structure 230 than the green or blue wavelengths.

Figure 3:
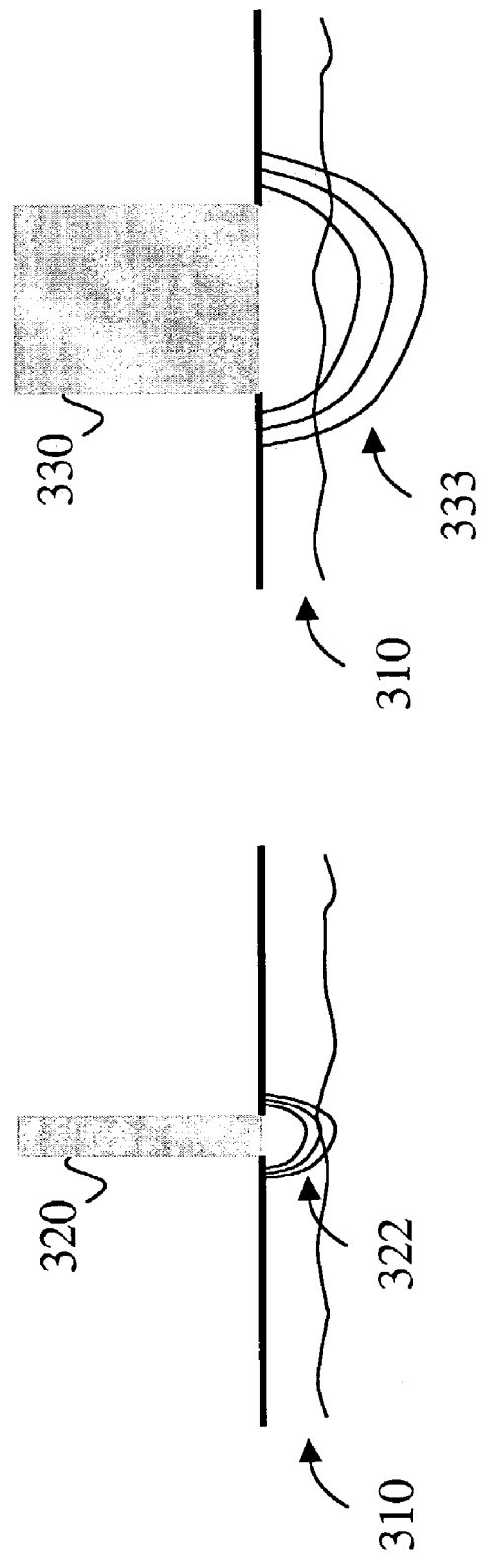
FIG. 3 shows an example of a fluence effect as a result of a small and a large light beam.

In addition, as it is known in the art, the relative subsurface fluence of a light beam in a structure 310 is dependent on the spot size, which could be relatively small 320 or relatively large 330, as shown in FIG. 3. The contour lines 322, 333 represent the relative subsurface fluences for identical fluences for the small 320 and large 330 spot size, respectively. The same subsurface fluence values appear at deeper levels with the larger 330 spot size compared to the smaller spot size 320.

Figure 4:
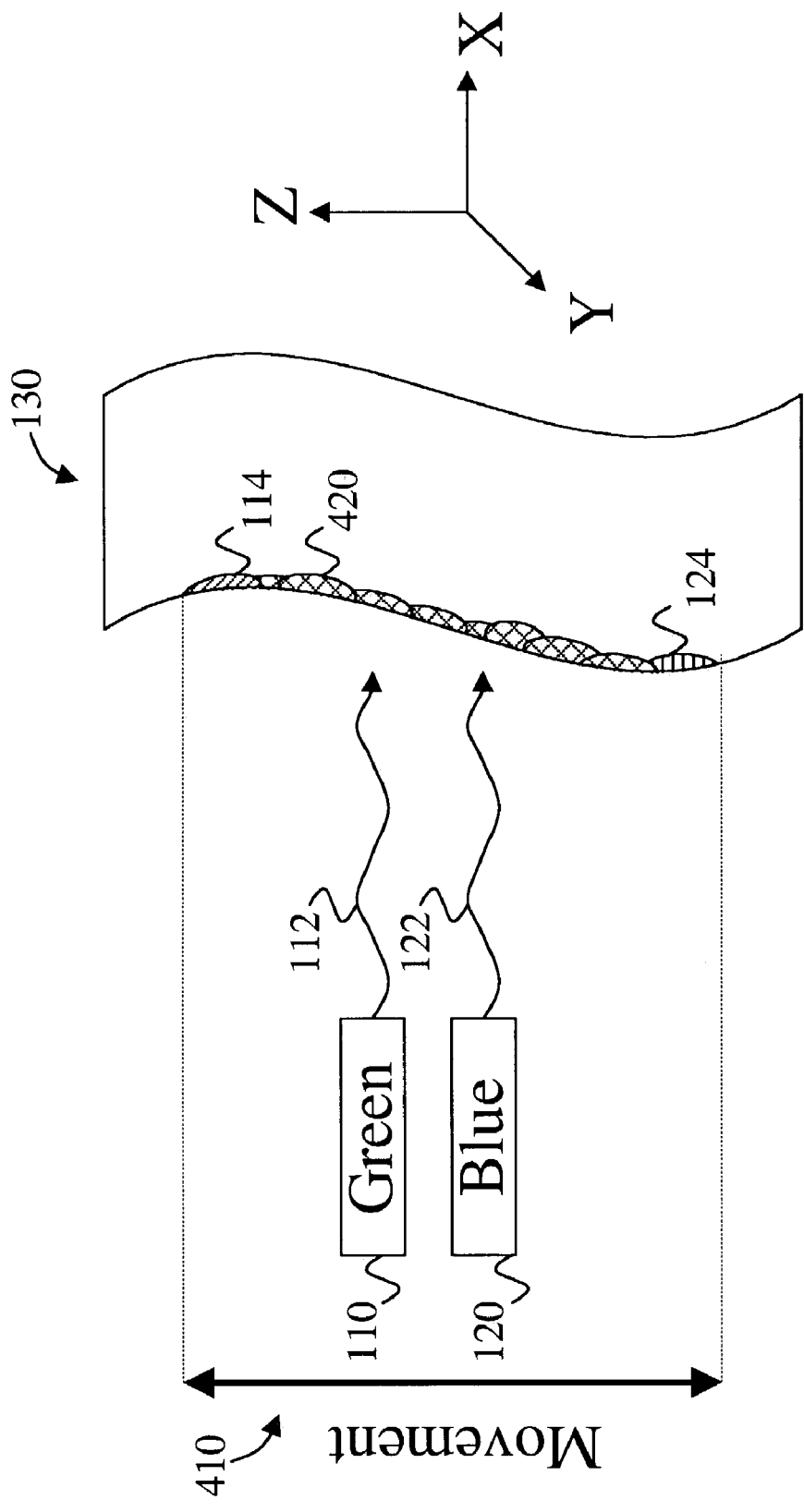
FIGS. 4–5 show examples of applying hygienic effects to structures in a dynamic manner according to the present invention.
Figure 5:
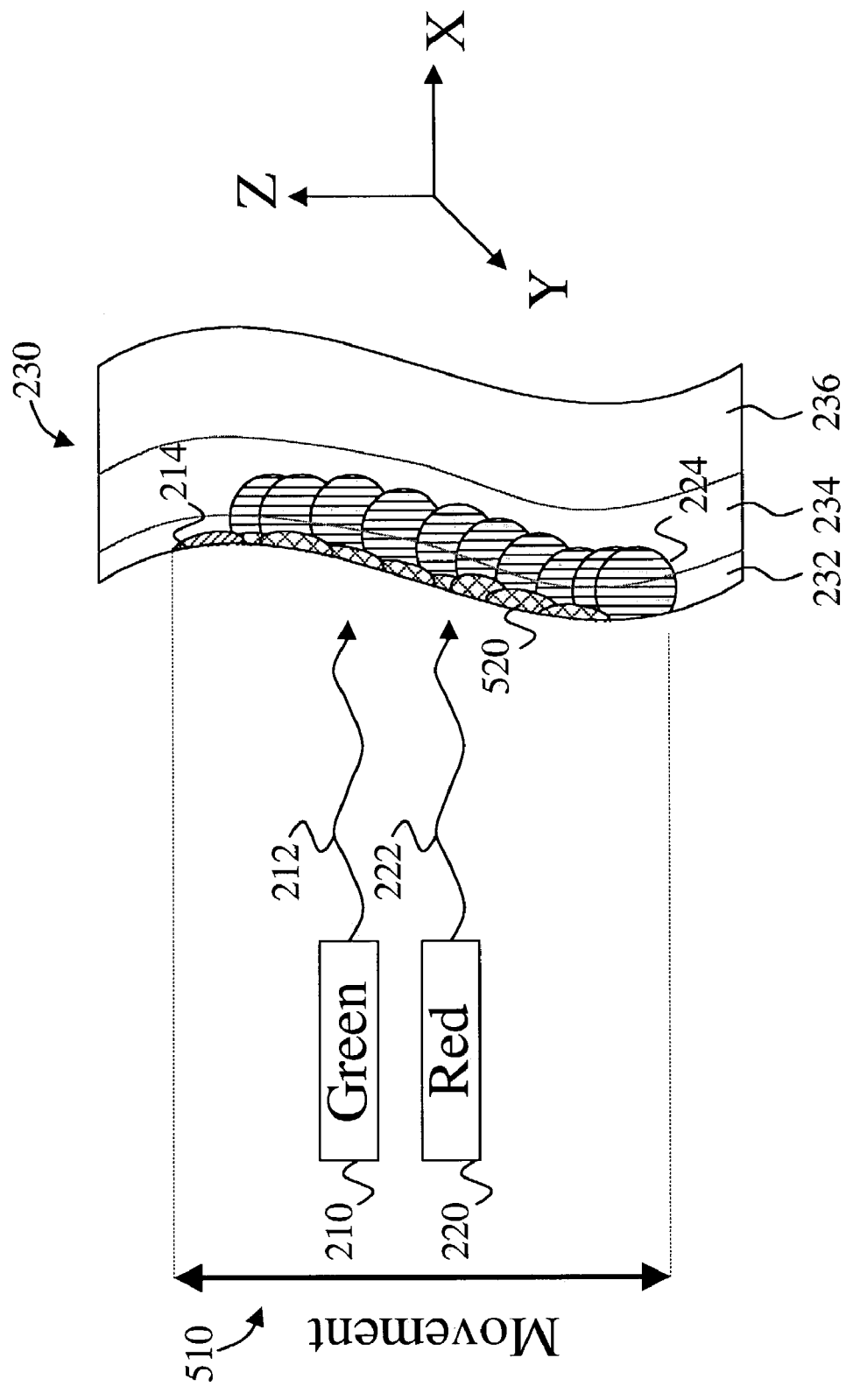

FIGS. 1–2 show exemplary embodiments of different hygienic effects in a structure in which the light beams are applied in a quasi-stationary manner. FIGS. 4–5 show exemplary embodiments of the application of hygienic effects as shown respectively in FIGS. 1–2, but now in a dynamic manner. Movement 410 of light sources 110, 120 concurrently applies the hygienic effects 114, 124 to different locations at structure 130 to achieve blending of these two unique hygienic effects at these different locations; 420 is an example of a blended hygienic effect of light beams 112, 124 as a result of movement 410, which is a blend of blue and green light. Movement 510 of light sources 210, 220 concurrently applies the hygienic effects 214, 224 to different locations at structure 230 to achieve blending of these two unique hygienic effects at these different locations where some of the areas of penetration overlap; 520 is an example of a blended hygienic effect of light beams 212, 224 as a result of movement 510, which is a blend of red and green light. Note that there are areas where the hygienic effects do not blend together due to different penetration areas, though these hygienic effects are applied in a concurrent fashion. The movement relative to structure 130 is not limited to movement 410, 510 (i.e. Z translation), but could be applied in X, Y, or Z direction (translation/rotation).

Figure 6:
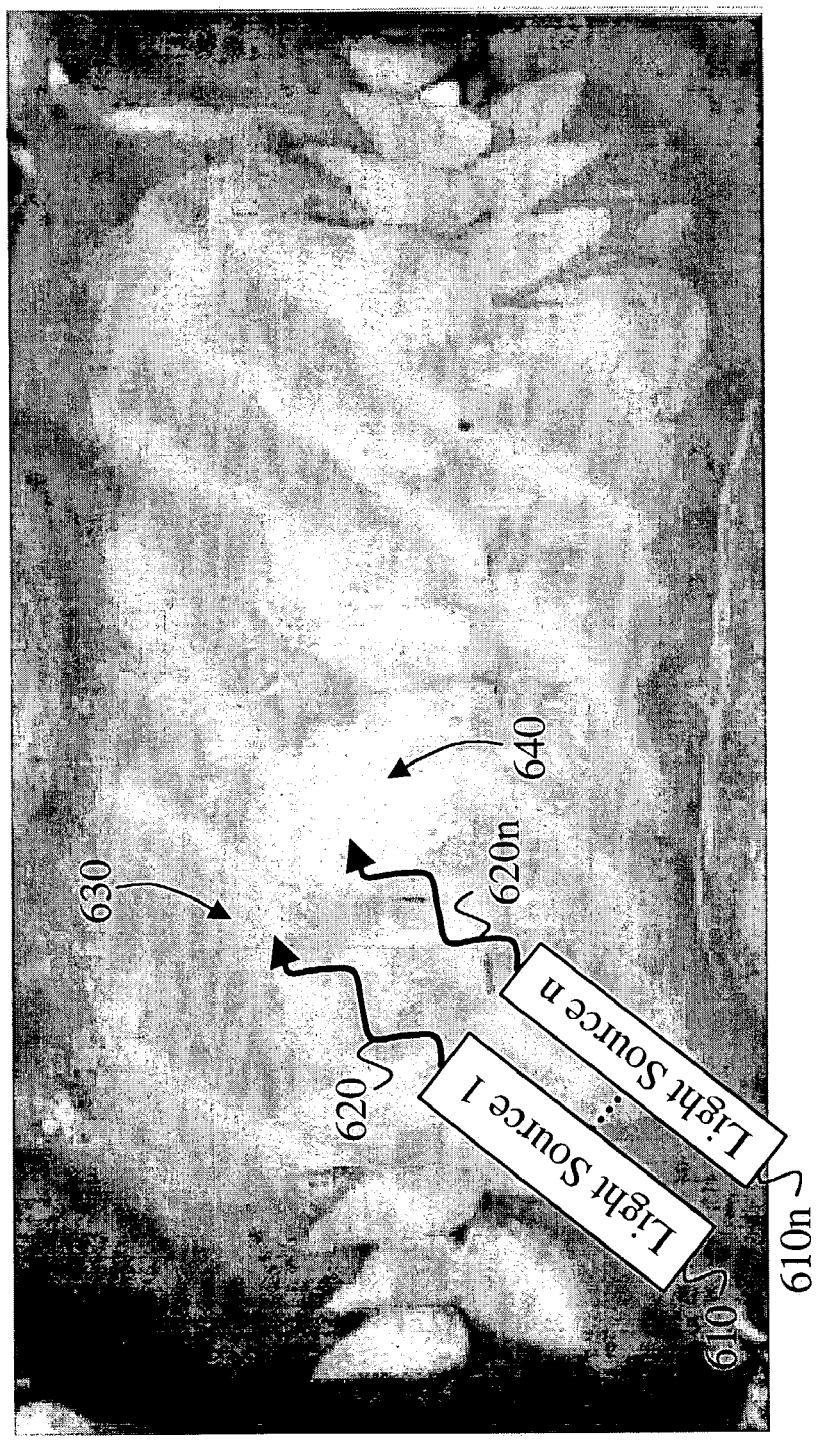
FIG. 6 shows an example of applying multiple hygienic effects to an oral cavity according to the present invention.

FIG. 6 shows an exemplary embodiment related to the application of a plurality of light beams 610 . . . 610n produced by light sources 620 . . . 620n. On the one hand, light beam 610 could provide one or more hygienic effects focusing on the gums 630 and could be selected as an anti-inflammatory effect, a periodontal or gum disease preventative effect, an anti-bacterial effect, a sterilizing effect, a cleaning effects, a therapeutic effect, a healing effect, a bio-stimulative effect, a bio-altering effect, a pain-releaving effect, a tissue rejuvenating effect, a photo-rejunivating effect, a photo-dynamic therapy effect and/or an agent penetrating effect. On the other hand, light beam 610n could provide one or more hygienic effects focusing on the teeth 640 and could be selected as a caries-protective effect, a sterilizing effect, an anti-bacterial effect, a tooth-whitening effect, an agent penetrating effect and/or a preventative effect. Again, as described supra, the application to the gums and teeth could be accomplished in a quasi-stationary manner, but preferably in a dynamic manner more or less similar to the movements related to tooth brushing.

Figure 7:
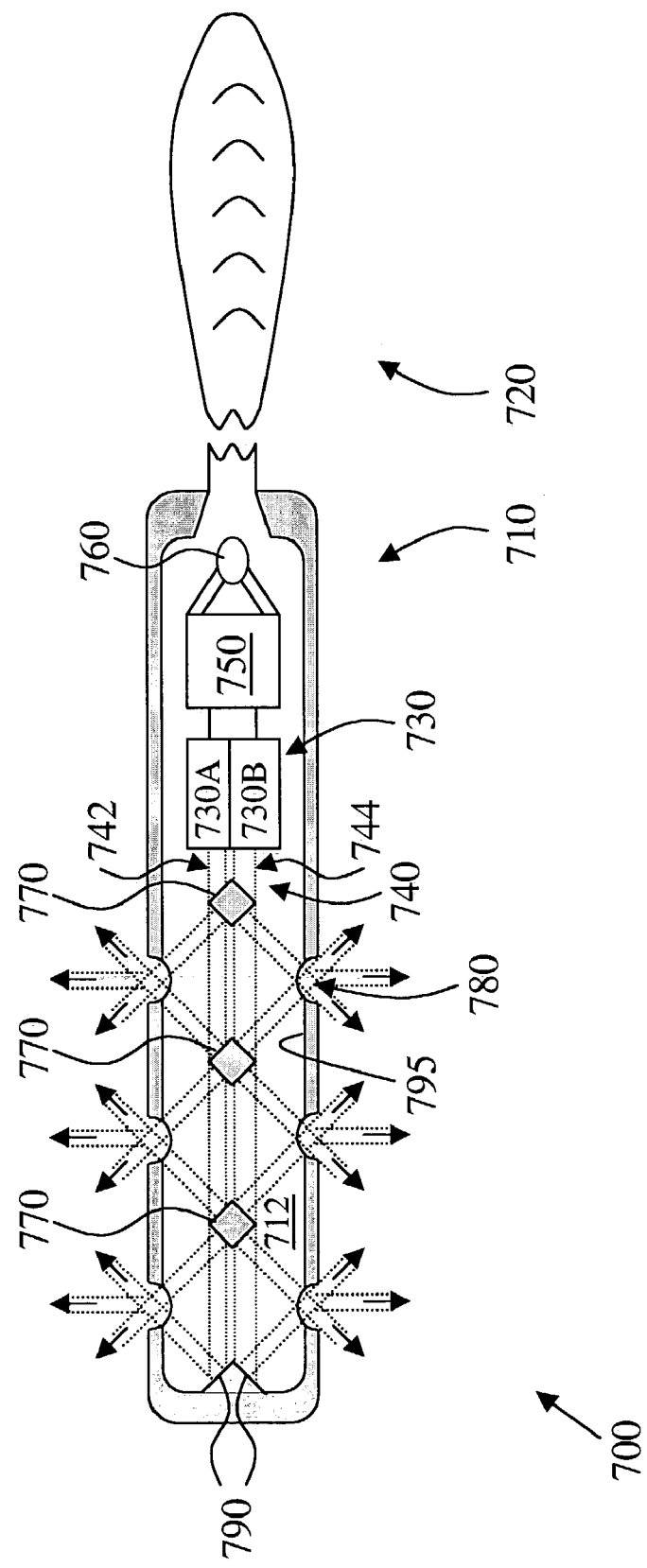
FIG. 7 shows an example of the device according to the present invention.

A first embodiment of a device of the present invention includes a head 710 and a handle 720 as shown by device 700 in FIG. 7. In one aspect, the handle and the head could be a single piece (not shown). However, in another aspect, as shown in FIG. 7, head 710 and handle 720 could be two separate parts of device 700, which would be preferred since it allows the user to replace the head with a new head or a different style head. The handle could take any shape and is not limited to the shape of handle 720 as shown in FIG. 7. However, it would be preferred to have an ergonomically shaped handle that easily fits in a user's hand. Different shapes and sizes of handles would then accommodate the shapes and sizes of the hands of children and adults. The inside 712 of head 710 includes two or more light sources 730 (i.e. 730A, 730B) and deliver light beams 740 with the desired hygienic effect as discussed supra. For illustrative purposes it could be assumed that there are two light sources delivering a light beam 742 with a first hygienic effect and a light beam 744 with a second hygienic effect. However, as described supra the present invention is not limited to two light sources. Light sources 730 are powered by a power supply 750, such as a battery. Power supply 750 is connected to a switch 760. Switch 760 is preferably positioned at the outside of head 720 and controls the on/off stage of power supply 750 and therewith the on/off stage of light sources 730. The inside 712 of head 720 includes an optical means to direct light beams 742, 744 from the inside of head 720 to the outside of head 720. As a person of average skill in the art to which this invention pertains would readily appreciate, this could be accomplished in different ways. To accomplish the output of light beams 742, 744 one could establish different optical means or pathways, which could include one or more optical components. Examples of such optical components, which are commonly available in the art, include optical fibers, lenses, spectral filters, mirrors, transparent materials, semi-transparent materials, prisms, reflective coatings, reflecting grooves, beam splitters, collimators, light channels and gratings.

In the example of FIG. 7, the optical means includes reflective prisms 770 to reflect and direct light beams 742, 744 in such a way that they are able to pass through openings 780 as shown in FIG. 7 (note that for clarity only one opening is indicated by 780). Optical means could include a main reflective prism 790 at the end of the optical pathway in head 720 to further assist in outputting light beams 742, 744. Likewise, the optical means at the inside of head 720 could further include a reflective coating 795 to assist in outputting light beams 742, 744. Openings 780 could be considered as part of the optical means. Openings 780 could define a spot size. Openings 780 could also include one or more optical components such as a lens, a transparent material a semi-transparent material, or the like.

Figure 8:
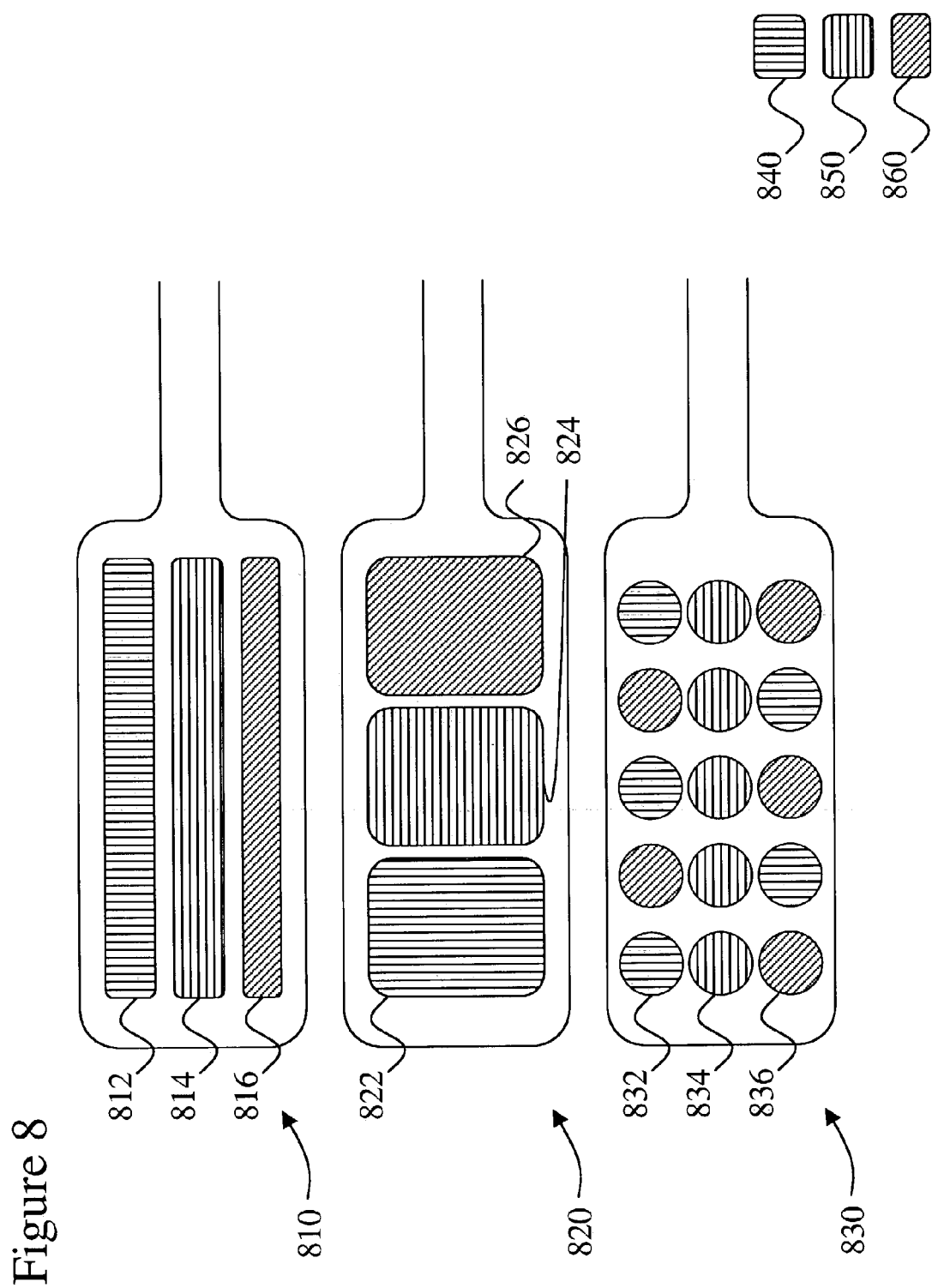
FIG. 8 shows examples of different configurations of the head of the device according to the present invention.

FIG. 8 shows different exemplary heads 810, 820 and 830 each with a different solution to outputting the light beams, which are shown for illustrative purpose only and should not be regarded as limiting to the invention. In the example of FIG. 8, three different hygienic light beams 840, 850, 850 are used. A first variation in the optical means could result in head 810 outputting light beams 840, 850, 850 through three rectangular shapes 812, 814, 816 distributed over head 810. Another variation in the optical means could result in head 820 outputting light beams 840, 850, 850 through three rectangular shapes 822, 824, 826 distributed over head 820. Yet another variation in the optical means could result in head 830 outputting light beams 840, 850, 850 through fifteen circular shapes 832, 834, 836 distributed over head 830 (note that only three circular shapes as indicated by 832, 834, 836 respectively). A consideration in the design of the optical outputs in a head relates to the ergonomics and ease of using the head when the hygienic effects are applied in a body cavity.

Figure 9:
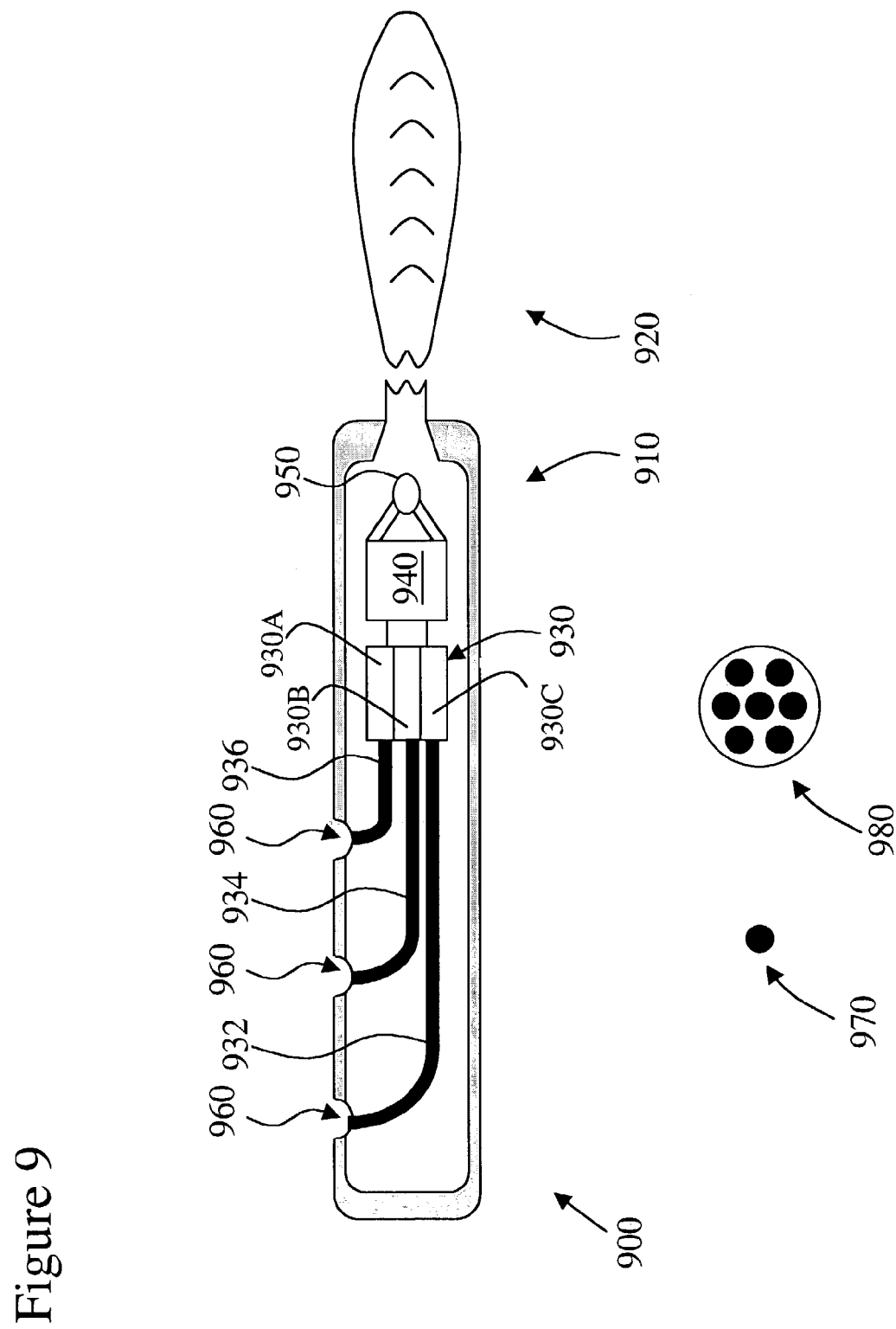
FIG. 9 shows another example of the device according to the present invention

A second embodiment of a device of the present invention is similar to device 700 as shown in FIG. 7 and is shown as device 900 in FIG. 9. Device 900 includes a head 910, handle 920, light sources 930 (i.e. 930A, 930B, 930C), power supply 940 and switch 950. The difference, however, between device 700 and device 900 is in the optical means. Device 900 includes optical fibers 932, 934, 936 that output the light beams from the light sources 930 through openings 960. In the example of device 900 there could be three light sources each delivering a light beam with a unique hygienic effect that is guided through optical fibers 932, 934, 936 respectively. There could be one optical fiber 960 connected to one opening or there could be several optical fibers bundled 970 together to output through one opening.

It has been shown that effect of radiation is improved in combination with massaging the gums. Pressuring alive soft tissue causes an increase in its transparacy thereby providing for better penetration of the radiation (See GA Askaryan (1982) in a paper entitled "*The increasing of transmission of laser and other radiation through the sift turbid physical and biological media*" and published in "*Kvantovaya Electronika*, V9(N7):1370–1383). The present invention generalizes this concept. Accordingly, the present invention could include a massaging means to massage the structure(s) in the body cavity and improve the transparency to the light beams. A first aspect of applying a massaging effect relates to the movement of the head or the pressure of the head against the structures in a body cavity will apply a massaging effect.

Figure 10:
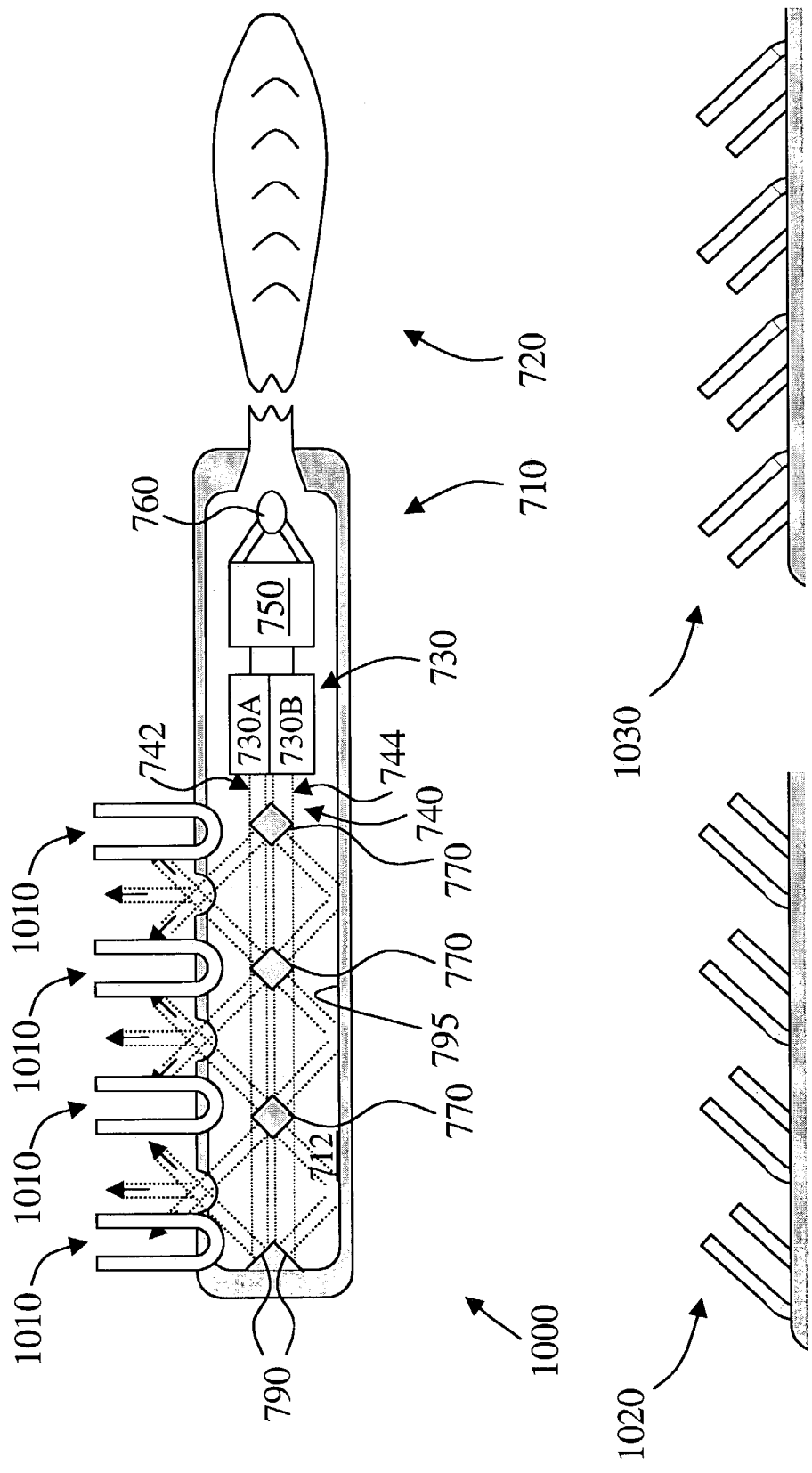
FIGS. 10–12 shows examples of the device with bristles according to the present invention.

FIG. 10 shows a second aspect of applying a massaging effect. Device 1000 is similar to device 700 with the difference of a massaging means 1010. Massaging means 1010 could be a plurality of bristles or a brush. The bristles could be positioned in any direction with respect to the handle. For instance, bristles could be positioned more or less perpendicular to the head as shown by bristles 1010 or bristles could be positioned under an angle with respect to the head as shown by bristles 1020 and bristles 1030. The direction of the bristles could depend on the type or shape of the head or the type of massaging effect that would be desired. The type and size of bristles is dependent on the type of body cavity, e.g. if an oral cavity is used then bristles like on a toothbrush would suffice. It would however be preferred to have flexible bristles that do not irritate or damage the structures. For instance, bristles could be made out of nylon, soft fiber, or any synthetic blend. The bristles could be attached to head 710 in a similar fashion as to how bristles are attached to a toothbrush head. Massaging means is used in a similar fashion as a toothbrush or a brush to add a massaging effect to the hygienic effect of the light sources.

Figure 11:
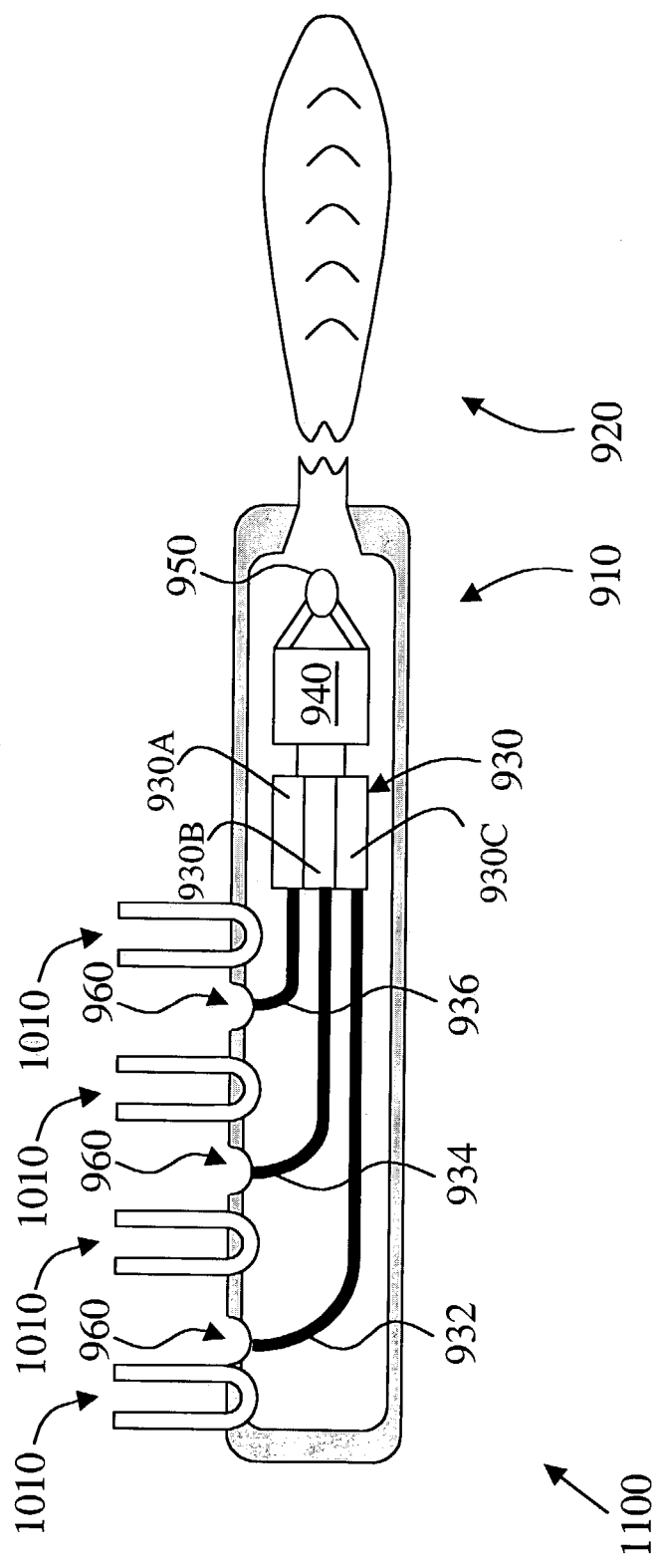
Figure 12:
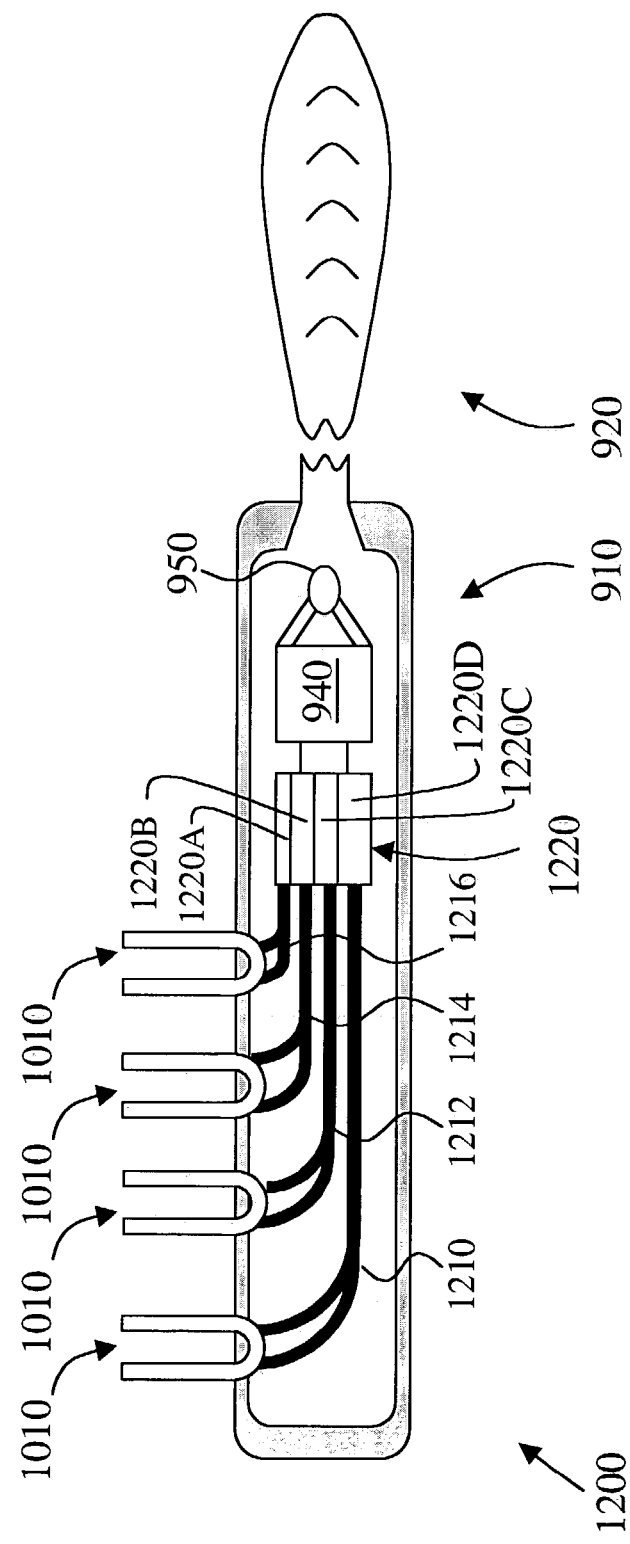

FIG. 11 shows a similar device 1100 as device 900 shown in FIG. 9 with the difference of the massaging means 1010. FIG. 12 shows device 1200, which is a variation of device 1100 as shown in FIG. 11. Device 1200 includes multiple optical fibers 1210 (2 fibers), 1212 (2 fibers), 1214 (2 fibers), 1216 (2 fibers) that transmit light beams from light source 1220 (including four light sources 1220A, 1220B, 1220C, 1220D). Another variation shown in FIG. 12 with respect to device 1100 is that the light beam does not pass through the openings 960 as shown in FIG. 9. Instead, an optical connection between the optical fibers and the bristles is created to establish that the bristles are able to continue to guide the light beams and finally output the light beams. In this case the bristles should be made out of materials capable of guiding light and flexible enough to prevent irritation or damage to the structures.

Figure 13:
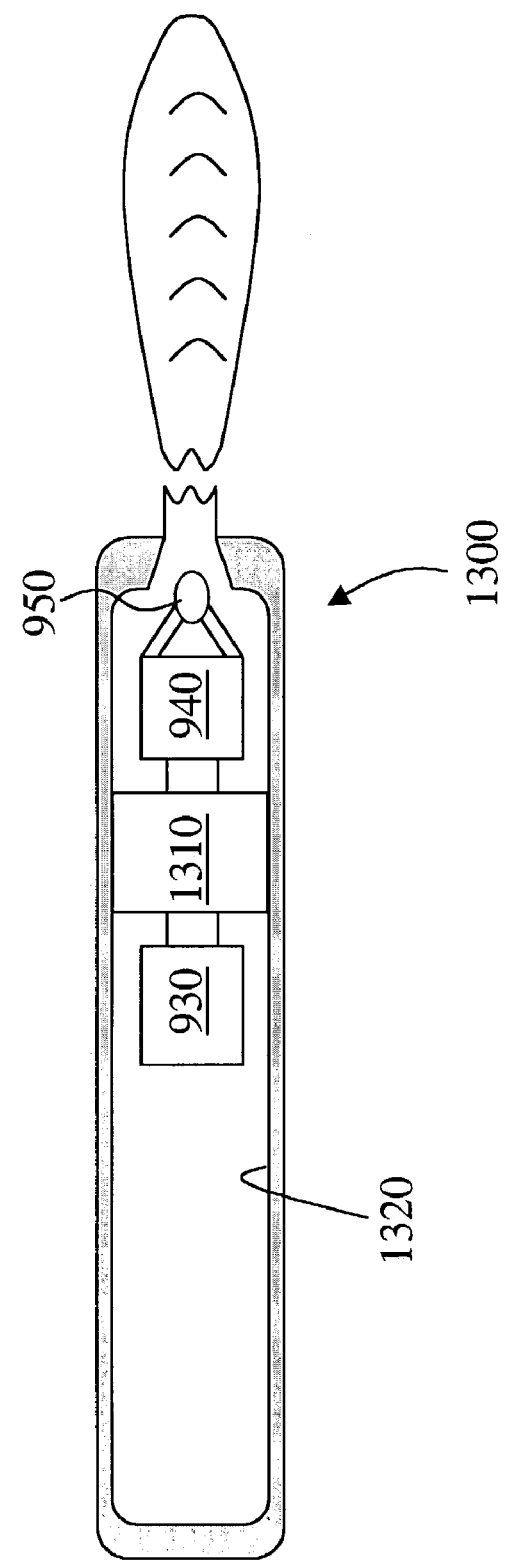
FIGS. 13–14 shows examples of the device with a vibrating means according to the present invention.
Figure 14:
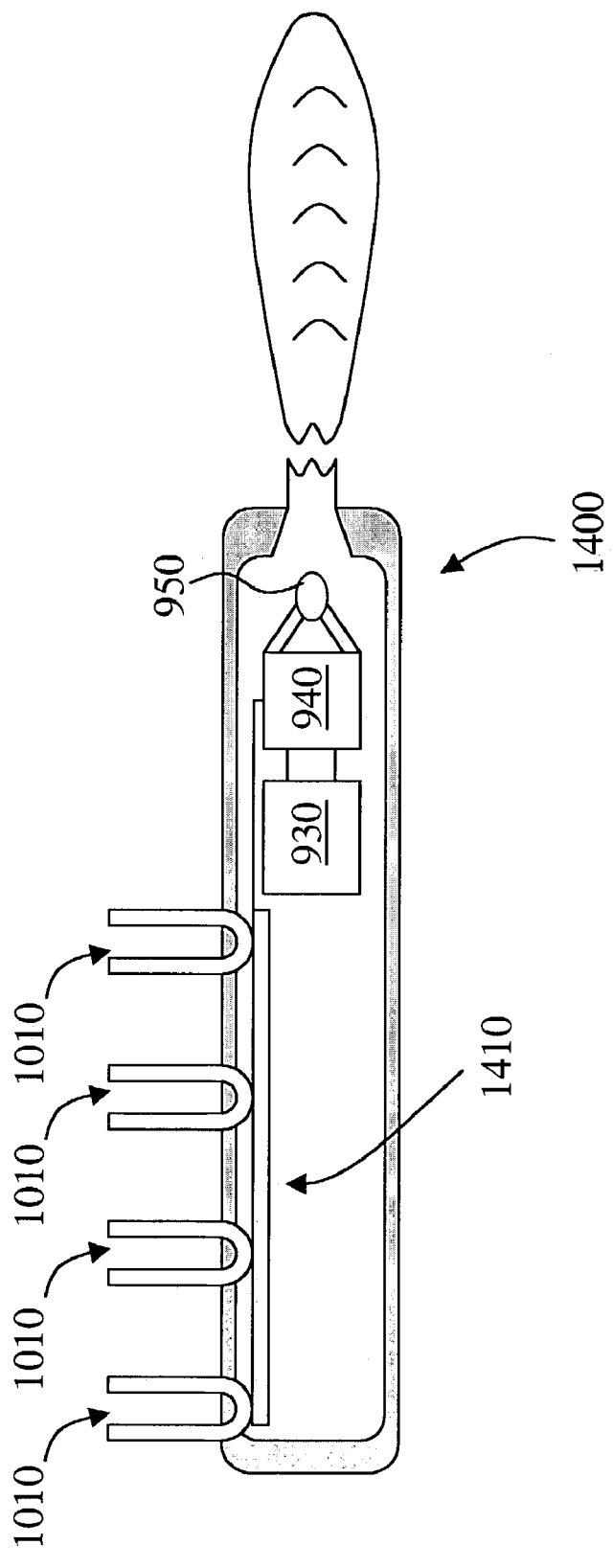

In another aspect, the present invention could include a vibrating means to vibrate the structures in the body cavity and therewith provide an additional massaging effect. Examples of vibrating means that could be used are an ultrasonic means, a piezoelectric means or a mechanical means. Such vibrating means are known in the art. FIG. 13 shows a head 1300 with a vibrating means 1310. Since vibrating means 1310 is positioned against the inner edge 1320 of head 1300, the entire head 1300 might vibrate. FIG. 14 shows a head 1400 with a vibrating means 1410 that is connected in such a way to vibrate the massaging means 1010, i.e. vibrating the bristles to provide an additional massaging effect to the massaging effect established by the bristles through movement as described supra.

Figure 15:
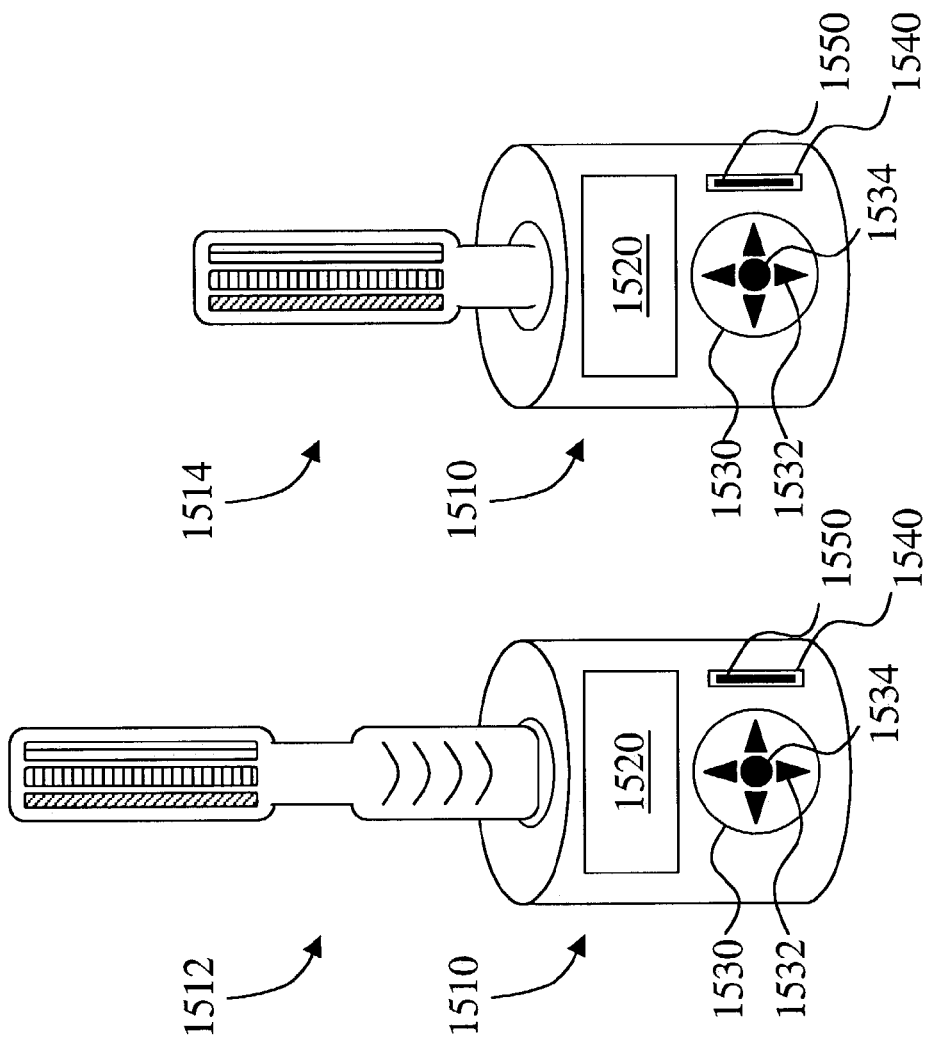
FIG. 15 shows the device in combination with a cradle according to the present invention.

FIG. 15 shows a cradle 1510 that can be used to store the hygienic device 1512 or the head 1514 of the hygienic device 1512. Cradle 1510 could also be used as a power supply (re)-charging device. In one aspect, hygienic device 1512 is placed in cradle 1510 and the power supply in the head is connected to a power recharging mechanism via the handle. In another aspect it would be possible to position the power supply of the hygienic device inside the handle, which is then directly connected to a power recharging mechanism. In yet another aspect, the head 1514 of the hygienic device is placed in cradle 1510 and the power supply in the head is directly connected to a power recharging mechanism.

Cradle 1510 could include a selection means 1540 for a user to select the hygienic effects or treatment parameters related to the unique hygienic effects. Selection means 1530 could be a selection means with, for instance, four arrow buttons 1532 and one center button 1534. Each arrow button 5132 corresponds to a function or selection that could be selected from a displaying means 1520. The up, down, left and right arrow buttons could relate to the browsing or selection from displaying means 1520. Displaying means 1520 could be any type or size of displaying means that would fit the cradle and is useful to the user. Necessary software and hardware components would be included to provide the functionality to display the parameters, selections and/or functions as well as provide functionality to the buttons. Center button 1534 could be used as the enter button to confirm a selection as is common in the art. The cradle could include different variations of a selection means and is not limited to the selection means shown by 1530.

Cradle 1510 could also include a slot 1540 for a read/writer card 1550 to read or write data. Examples of read/writer card 1550 are for instance a memory stick, compact flash card, smart media card, secure digital card, multi media card, microdrive or the like, which are common in the art. Read/writer card 1550 can upload information to the device, store information from the device, and could be interactively used with any type of hygienic service provider as described infra.

Figure 16:
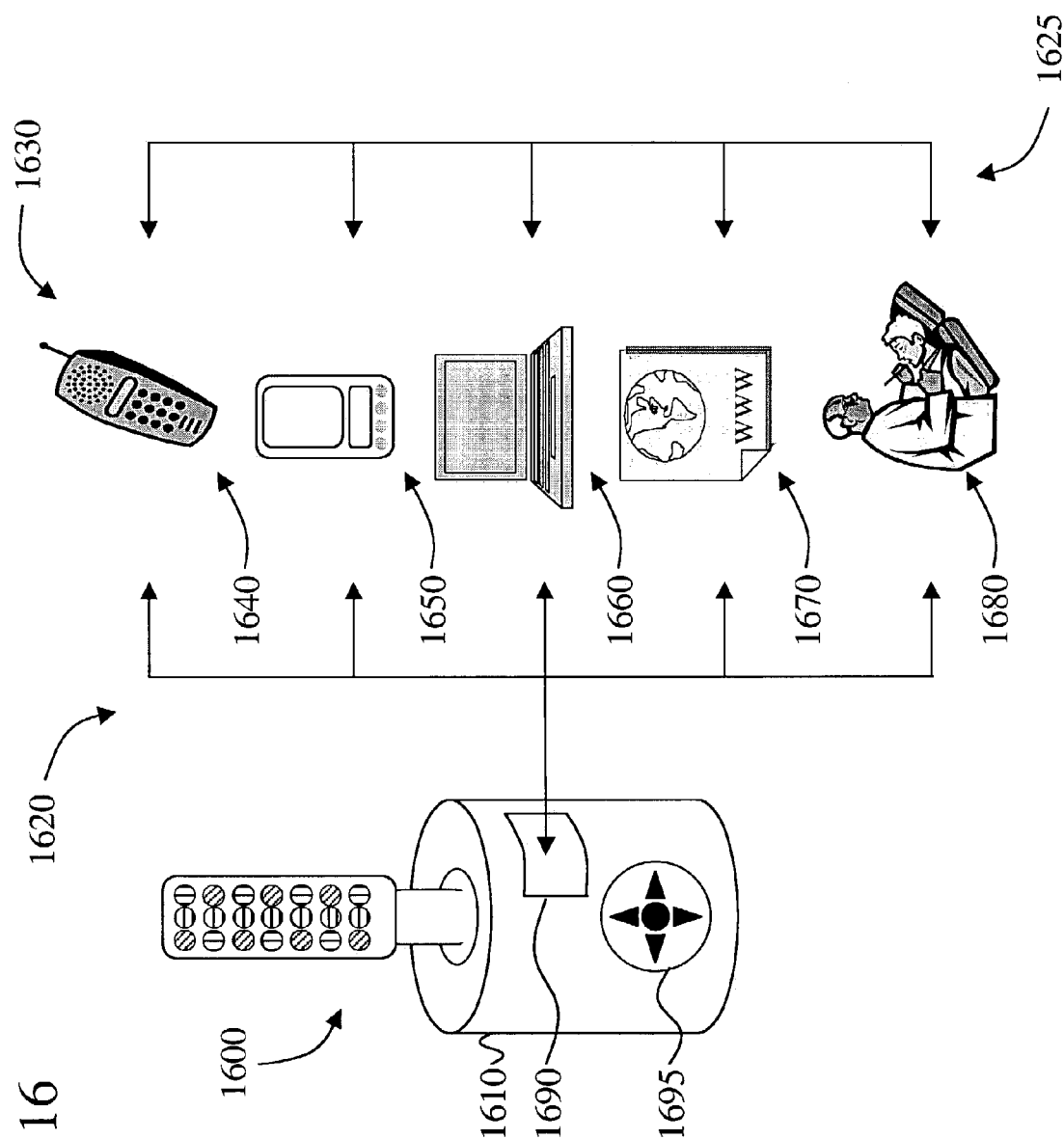
FIG. 16 shows the device with a communication means to communicate with hygienic service providers.

FIG. 16 shows a system of a hygienic application device 1600 positioned in a cradle 1610 that could communicate 1620 with a hygienic service provider 1630. Hygienic service provider 1630 includes a cell phone 1640, a personal digital assistant, a Pocket PC or a handheld communication device (all three shown by 1650), a computer 1660, an Internet website 1670 or a professional service 1680 (e.g. a dentist, a medical doctor, a pharmaceutical company, medical company, or the like). The hygienic service provider 1630 provides information related to the hygienic application device 1600 that could be communicated 1620 back and forth between hygienic application device 1600 and hygienic service provider 1630. Furthermore, the individual hygienic service providers 1630 could interact and communicate with each other 1625. For instance, one could use Internet website 1670 and relay the data to cell phone 1640 before communicating with hygienic application device 1600. Several different scenarios are possible and would provide flexibility to the user to obtain and provide data related to their hygienic treatment(s) that are used by hygienic application device 1600. The communications means that could be used includes any wireless or wired communication means as common and available in the art. Furthermore, hygienic application device 1600 could include IR port, RF link, Bluetooth, phone line or Ethernet port or any type of wireless or wired communication means (shown by 1690) suitable to communication with hygienic service provider 1630. Selection means 1695 could be used as a means to send data from hygienic application device 1600 to hygienic service provider 1630 in a similar fashion as the HotSync key on Personal Digital Assistants (PDAs). Read/writer card 1550 as shown in FIG. 15 could also be used as communication means 1620, 1625.

Figure 17:
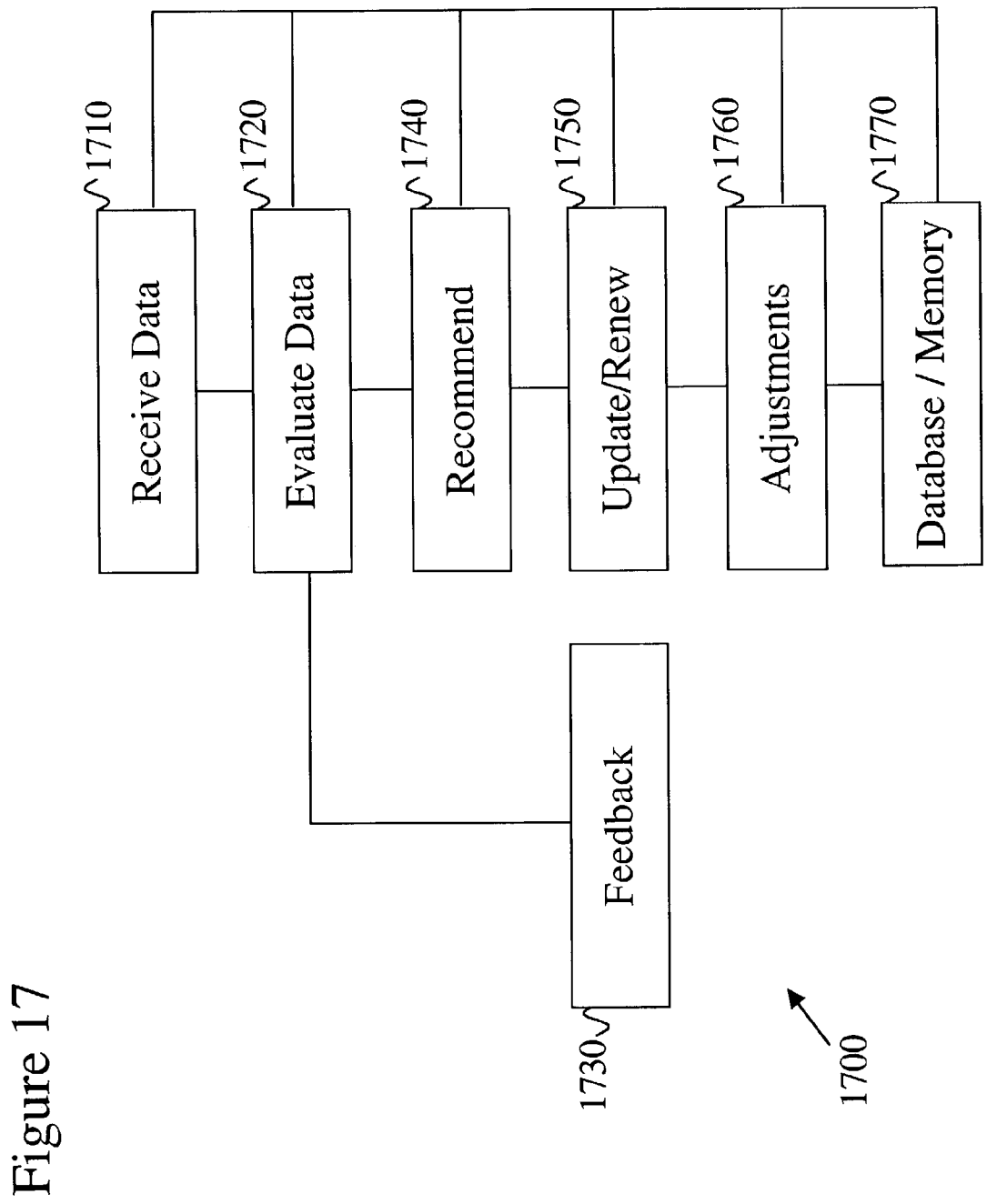
FIG. 17 shows an example of additional device means and methods steps according to the present invention.

A method 1700, preferably implemented through software, could be included that receives data 1710 that can be evaluated 1720 as shown in FIG. 17. Note that there is no limitation to where software program 1700 could be running which could be on hygienic application device 1600 and/or on any of the hygienic service providers 1630. The evaluation could relate to the evaluation of the hygienic treatment plan. The hygienic treatment plan could be evaluated based on whether it needs an update or whether it needs to be renewed. The evaluation could also relate to the evaluation of the performance and quality of the device, for instance, to determine if the light sources and light beams still meet certain performance or quality requirements. This could be determined after testing or calibration of the hygienic application device 1600 as described infra). The evaluation could further relate to the evaluation of user feedback about the application of the hygienic treatment plan (e.g. determined through a questionnaire as described infra). Based on the evaluation 1720 feedback could be generated 1730 to inform the user about an update, status of the treatment plan, new information, status of the device, or the like. To provide feedback, the hygienic application device 1600 could include a feedback means to provide feedback to a user. Examples of feedback that is useful relate to sound, display on the displaying means (See FIG. 15) or vibration and could be produced from a means situated in the hygienic application device 1600 or from a means in cradle 1610. Also based on the evaluation 1720 a recommendation 1740 could be provided to update or renew 1750 the hygienic treatment plan and/or its corresponding parameters. Adjustments 1760 could be made to the treatment plan as well as to the hygienic device itself, for instance to adjust the power level of the light source to meet performance requirements for a hygienic effect. Adjustments could be made at the software level or at the hardware level such as on a microchip. Appropriate hardware and/or software will be included to make the desired adjustments possible. Performance data, data related to evaluations, data related to recommendations, data related to updates or renewals, data related to adjustments, or feedback data or the like could be stored in a memory 1770. Memory 1770 could be accessed by a software/hardware interface (as common in the art) to retrieve or store data. Memory 1770 could include a microchip, a database (software/hardware coded), or any other data storage or memory device common in the art.

Figure 18:
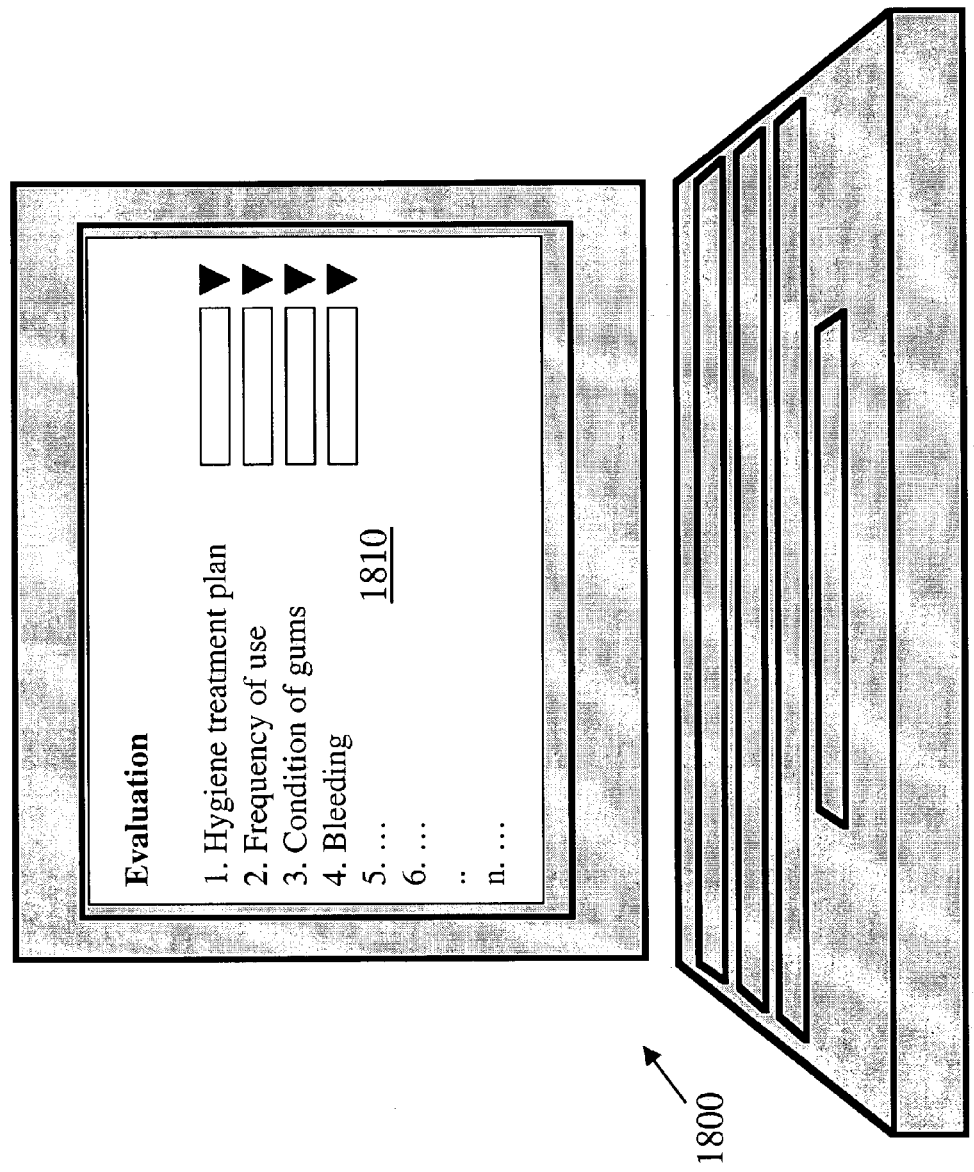
FIG. 18 shows a computer with an evaluation according to the present invention.

FIG. 18 shows an exemplary embodiment of an evaluation 1810 that a user could fill out on a computer 1800. The evaluation could include a list of questions related to the currently used hygienic treatment plan such as the type of hygienic treatment that is used, the frequency of use, condition of the gums if the plan related to oral hygienic treatment, bleeding, or the like. As a person of average skill would appreciate this list of questions could vary and is dependent on the type of hygienic treatment that is used. In addition the particular user interface to pose the questions and answer the questions could include, without any limitations, radio buttons, text boxes, click boxes, sliders, or touchscreen selections. The evaluation could take place on cell phone 1640, personal digital assistant, a Pocket PC or a handheld communication device (all three shown by 1650), computer 1660 or Internet website 1670.

Figure 19:
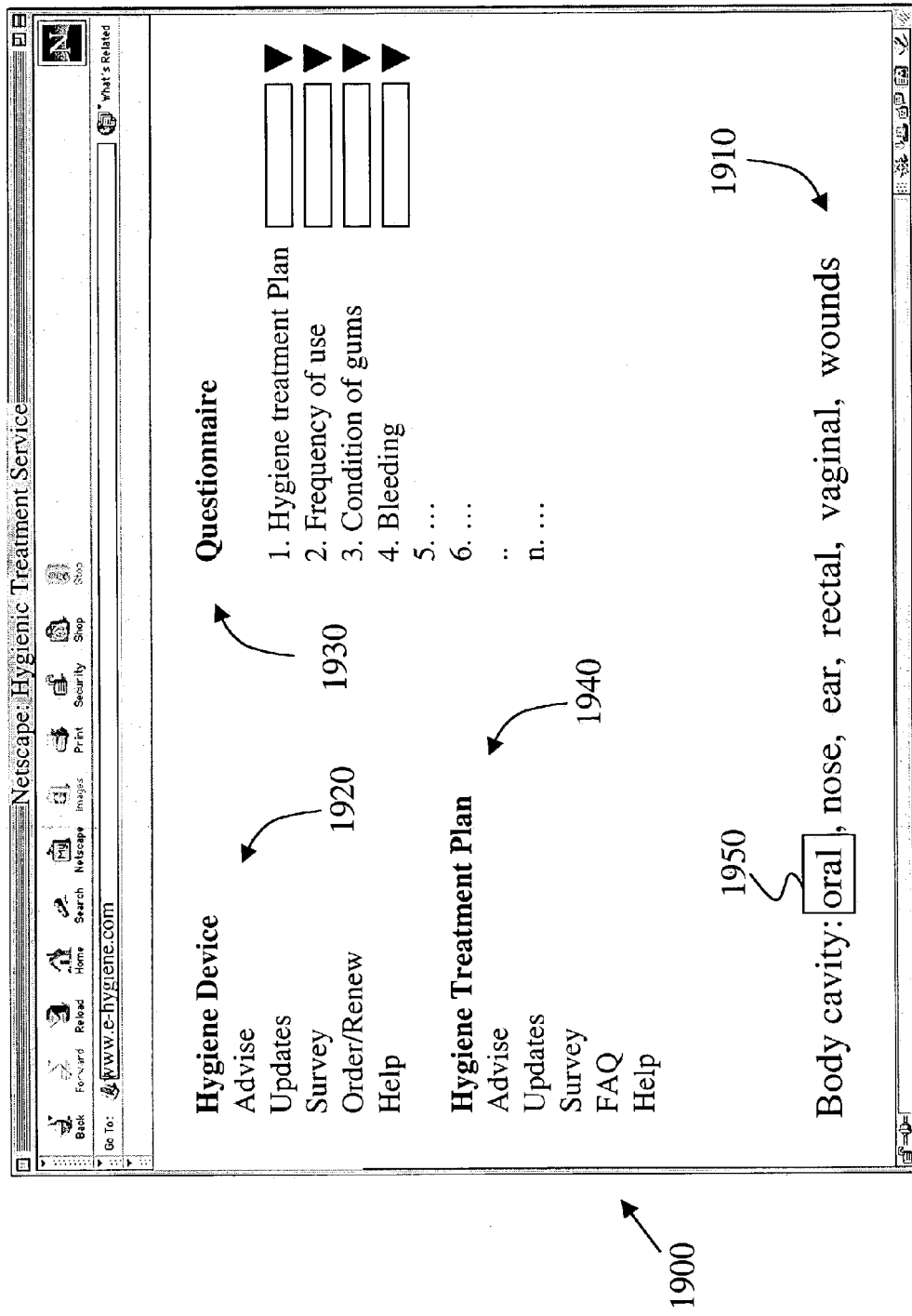
FIG. 19 shows a website of a hygienic service provider providing hygienic services according to the present invention.

FIG. 19 shows an embodiment of how a user could interact with a hygienic service provider related to particular body cavities 1910. An interactive website 1900 is used that could be displayed on cell phone 1640, personal digital assistant, Pocket PC or handheld communication device (all three shown by 1650) or computer 1660. Such a site could provide information to the user related to hygienic application device 1920 (such as advise, updates, survey/questionnaire 1930, order/renew, help, etc.) or related to specifics of a hygienic treatment plan 1940 (such as advise, updates, survey/questionnaire 1930, frequently asked questions (FAQ), help, etc.). The particular example of interactive website 1900 shows a selection of an oral cavity 1950, but could easily be created for other body cavities such the ear, nose, rectal, vaginal, wounds, etc., listed by 1910. As a person of average skill would appreciate the layout of the website and content of the website could vary and is dependent on the type of hygienic treatment that is used. In addition the particular user interface to pose the questions and answer the questions could be based, without any limitations, on any type of website design language (e.g. HTML, XML, Java, Flash, or the like).

Figure 20:
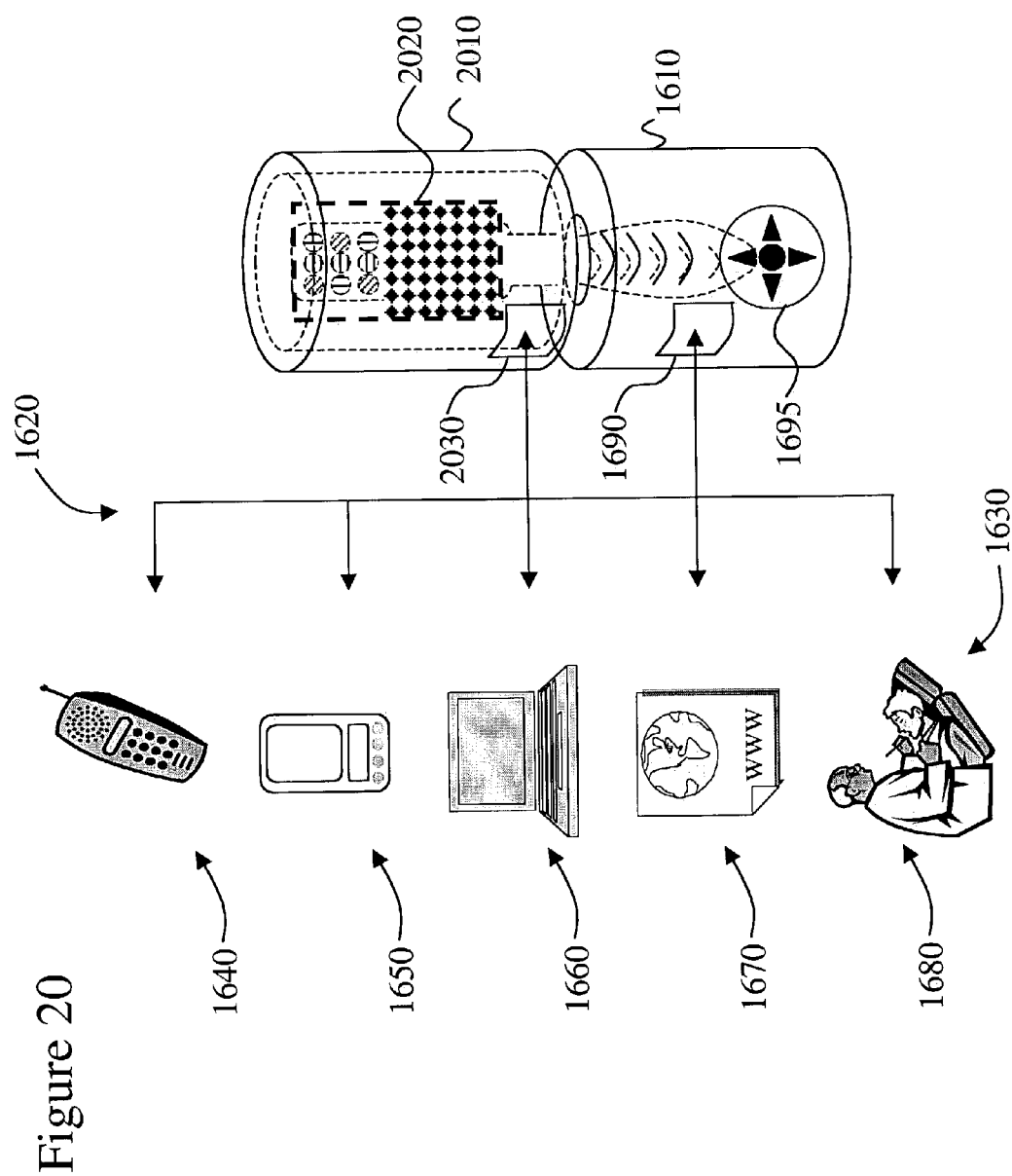
FIG. 20 shows a test or calibration device that can be used to test or calibrate the hygienic device according to the present invention.
Figure 21:
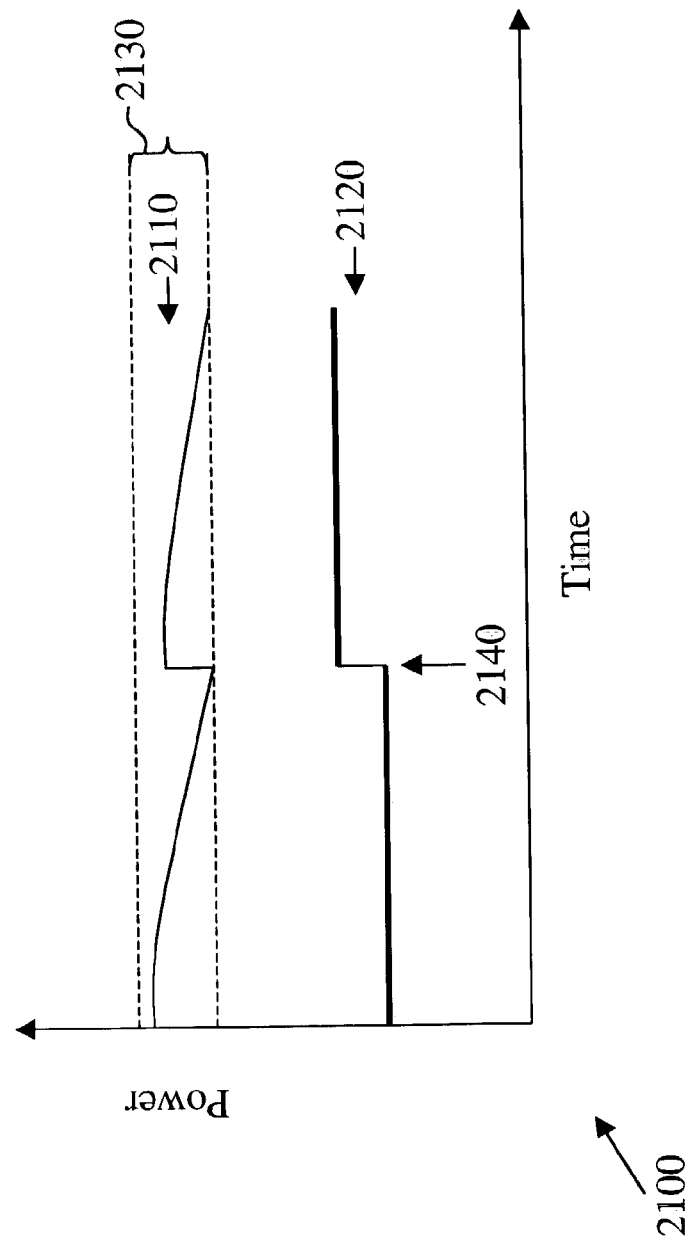
FIG. 21 shows a performance evaluation according to the present invention.

FIG. 20 shows a hygienic device positioned in cradle 1610 and with communication means 1620 to communicate with hygienic service providers 1630 in a similar fashion as shown in FIG. 15. The addition in FIG. 20 is that a testing means 2010 is included that allows one to test or calibrate the hygienic device in terms of its performance of delivering quality hygienic effects according to set standards. The idea is to test or calibrate for instance the power output or light beams, and determine whether their respective parameters would still fall within the performance or quality requirement(s) specified for a hygienic treatment plan. This way it could be ensured that the hygienic treatment plan is still working appropriately, and if not whether to make the appropriate adjustments 1760, to provide feedback 1730 to the user or hygienic service provider 1630, to renew, update one or more device components or parameters of the treatment plan. FIG. 21 shows an example 2100 of a power level 2110 of a light beam generated by a light source (the generation is shown by 2120). It is shown that over time power level 2110 drops under a performance range 2130, possibly due to deterioration of device component(s). Power generation 2120 to the light source can be adjusted 2140 over time to ensure a more or less constant power output. Different strategies, discrete or continuous, could be employed to adjust a particular parameter and adjust toward a desired performance level.

In the example of FIG. 20, testing means 2010 is shown as an up-site down cup that is placed over the handle. Inside the cup could be circuit 2020 with sensors, a microchip, spectroscopic means and data acquisition means capable to detect and analyze the output by the light beams. Such sensors, spectroscopic means and data acquisition means are common in the art which could all be included as means to provide testing means 2010 (See, for instance, the following companies which are listed for purposes of illustration and should not be regarded as limiting to the invention: Minco Products Inc., Minneapolis, Minn.; Key Instruments Inc., Trevose, Pa.; Colimetric fiber optic sensors by Eltron Reaearch Inc.; Ophir Optronics Inc., Danvers, Mass.; Ocean Optics BV, Duiven, The Netherlands; or ultrathin data acquisition system by Nielsen Engineering and Research NEAR). The data obtained from the testing means could be communicated through a separate communication link 2030 or through communication link 1690 of cradle 1610 provided that there is a link between the testing means 2010 and cradle 1610. As described supra with respect to FIGS. 16–17 the test or calibration data could be evaluated upon which feedback could be provided, a recommendation could be made or an adjustment to the control of the device could be made.

Figure 22:
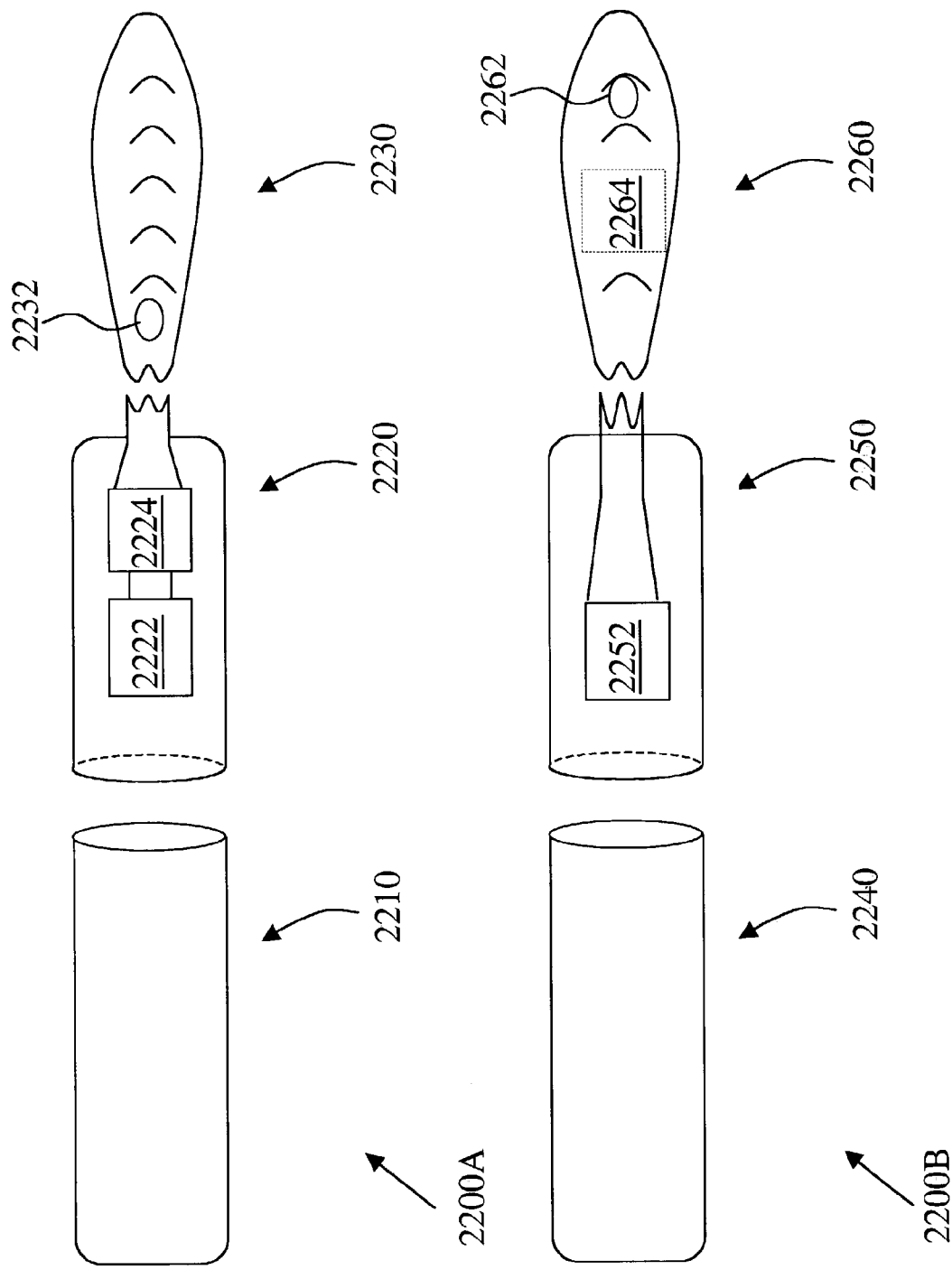
FIG. 22 shows detachable components of the device according to the present invention.
Figure 23:
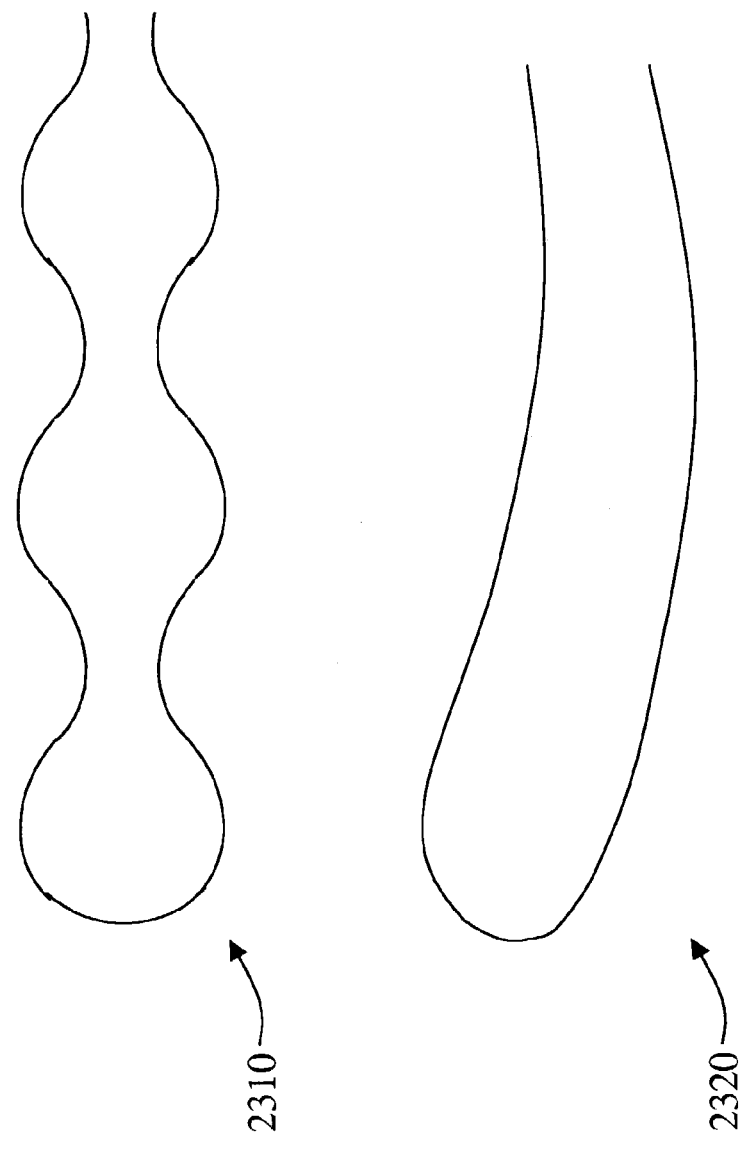
FIG. 23 shows different exemplary shapes of the head of the hygienic device according to the present invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, the hygienic device of the present invention could be a handheld device. Furthermore, the hygienic device could have several removable or detachable components, which would allow these components to be changed, renewed or updated. For example, the components could be disposable components, or even recyclable components. FIG. 22 shows some examples 2200A, 2200B of configurations of detachable components of the hygienic device, which are shown for illustrative purposes only and should not be regarded as limiting to the invention. Device 2200A shows a head 2210 for optical guidance and output of the light beams, a mid-component 2220 hosting the light sources 2222 and the power supply 2224, and a handle 2230 with a switch 2232. Device 2200B shows a head 2240 for optical guidance and output of the light beams, a mid-component 2250 hosting the light sources 2252, and a handle 2260 with a switch 2262 and a power supply 2264. Another variation to the hygienic device is the shape of the device; in particular the shape of the head component or the head and mid-components combined. FIG. 23 shows two examples of shapes that could be used, which are shown for illustrative purposes only and should not be regarded as limiting to the invention. Shape 2310 has an irregular but smooth surface that would for instance be desired to enhance the massaging effect or contribute to the output path of the light beams. Shape 2320 has a banana-like or curved shape and would for instance be desired to approach particular body cavities that are difficult to access with a more rectangular shaped-component or device. Yet another variation is that an agent could be used and applied to the structures of the body cavity before, during or after the application of the hygienic treatment. Examples of agents are for instance bioprotective agents, photocatalyst, treatment gels or cream, soothing agents, skin permeation enhancers or the like (See, for instance, the following companies/products which are listed for purposes of illustration and should not be regarded as limiting to the invention: Neova by Procyte Corp. www-.procyte.com; Medicalia Inc. www. medicalia. com; or ESBA Laboratories Inc.). Such agents could work as a catalyst, soother or enhancer to the structures. Still another variation relates to verifying the condition of the structures of a body cavity before, during or after a hygienic treatment is applied. Such a diagnostics for structures could, for instance, be employed by means of spectroscopy resolved fluorescence (See e.g. Pferer et al. (2003) in a paper entitled "*Temporally and spectrally resolved fluorescence; spectroscopy for the detection of high grade dysplasia in Barrett's esophagus*" and published in "*Lasers in Surgery and Medicine* 32:10–16). Diagnostics of the structures could provide valuable information to evaluate and compare the efficacy of the hygienic treatment. All such variations are considered to be within the scope and spirit of the present invention as defined by the following claims and their legal equivalents.

What is claimed is:

1. A brush to concurrently apply two or more hygienic effects to structures in a body cavity, comprising:
   (a) a handle;
   (b) a head with two or more light sources each delivering a unique light beam having a unique hygienic effect;
   (c) multiple openings through the surface of said head, said multiple openings sized to output each at least one of said light beams and said openings spaced to guide and maintain said light beams to avoid diffusion of said light beams before said light beams arrive at the structures in said body cavity; and
   (d) bristles distributed at the surface of said head.

2. The brush as set forth in claim 1, wherein said light sources are low power lasers, light emitting diodes or semiconductor lasers.

3. The brush as set forth in claim 1, wherein said hygienic effect is selected from the group consisting of an anti-inflammatory effect, a preventative effect, a caries-protective effect, an anti-bacterial effect, a sterilizing effect, a cleaning effect, a cosmetic effect, a therapeutic effect, a healing effect, a bio-stimulative effect, a bio-altering effect, a pain-releaving effect, an agent penetrating effect, a photo-rejuvinating effect and a photo-dynamic treatment effect.

4. The brush as set forth in claim 1, wherein said light beam comprises light from the ultraviolet, visible or infrared spectrum.

5. The brush as set forth in claim 1, wherein said body cavity comprises an oral system, a nasal system, an ear, a rectal system, a vaginal system, a uterus, an open wound, or a surgically created body cavity.

6. The brush as set forth in claim 1, further comprises optical pathways having one or more optical components wherein said one or more optical components are selected from the group consisting of optical fibers, lenses, spectral filters, mirrors, transparent materials, semi-transparent materials, prisms, reflective coatings, reflecting grooves, beam splitters, collimators, light channels and gratings.

7. The brush as set forth in claim 1, further comprising a means for massaging said structures in said body cavity.

8. The brush as set forth in claim 1, further comprising a means for vibrating said structures in said body cavity, wherein said means for vibrating comprises an ultrasonic means, a piezoelectric means or a mechanical means.

9. The brush as set forth in claim 1, further comprising a means for communicating data with a cell phone, a personal digital assistant, a Pocket PC, a computer, an Internet website, a professional or a service.

10. The brush as set forth in claim 9, wherein said data comprises data related to said unique hygienic effects or data related to said device.

11. The brush as set forth in claim 1, further comprising a means for testing a performance of said device.

12. The brush as set forth in claim 11, further comprising a means for adjusting one or more components based on said test.

13. The brush as set forth in claim 1, further comprising a means to provide feedback to a user, wherein said feedback is selected from the group consisting of sound, display and vibration.

14. The brush as set forth in claim 1, further comprising a means for selecting by a user parameters related to said unique hygienic effects or related to said light beams to a user.

15. The brush as set forth in claim 1, further comprising a display means to display data related to said unique hygienic effects or related to said light beams to a user.

16. The brush as set forth in claim 1, further comprising a cradle for hosting said handheld device, wherein said cradle comprises means for communication, means for power recharging, means for selecting a hygienic program, a display, a storage medium or a means for testing said handheld device.

17. The brush as set forth in claim 1, further comprising a controller to control simultaneous output of at least two of said unique light beams.

18. A brush to concurrently apply two or more hygienic effects to structures in a body cavity, comprising:
   (a) a detachable handle; and
   (b) a detachable head with two or more light sources each delivering a unique light beam having a unique hygienic effect;
   (c) multiple openings through the surface of said head, said multiple openings sized to output each at least one of said light beams and said openings spaced to guide and maintain said light beams to avoid diffusion of said light beams before said light beams arrive at the structures in said body cavity; and
   (d) bristles distributed at the surface of said head.

19. The brush as set forth in claim 18, wherein said detachable head comprises at least two detachable components, wherein a first component comprises light sources that generate said light beams and wherein a second component comprises optical pathways.

20. The brush as set forth in claim 19, wherein said at least two detachable components are disposable components.

21. The brush as set forth in claim 18, wherein said detachable handle is a disposable handle.

22. The brush as set forth in claim 18, wherein said detachable head is a disposable head.

23. The brush as set forth in claim 18, further comprising a controller to control simultaneous output of at least two of said unique light beams.

24. A system to provide a hygienic service to body, comprising:
  (a) a hygienic service provider to provide parameters for a hygienic treatment including at least two or more unique hygienic optical treatment effects;
  (b) brush having bristles distributed at its surface head, openings spaced to minimize or avoid blending of multiple light beams and guide said multiple light beams to separately arrive at the structures of said body structures and a controller for simultaneously applying said hygienic treatment having said at least two or more unique hygienic treatment effects to said body structures; and
  (c) a means for communicating said parameters between said hygienic service provider and the controller of said hygienic application device.

25. The system as set forth in claim 24, wherein said hygienic service provider comprises a cell phone, a personal digital assistant, a Pocket PC, a computer, an Internet website, a professional or a service.

26. The system as set forth in claim 24, said hygienic service provider comprises means to evaluate said parameters.

27. The system as set forth in claim 24, said hygienic service provider comprises a means to recommend said parameters.

* * * * *